(12) United States Patent
Ishihara

(10) Patent No.: US 8,193,517 B2
(45) Date of Patent: Jun. 5, 2012

(54) FLUOROSCOPY SYSTEM, FLUOROSCOPY APPARATUS, AND FLUOROSCOPY METHOD

(75) Inventor: Yasushige Ishihara, Tokyo (JP)

(73) Assignee: Olympus Corporation, Tokyo (JP)

(*) Notice: Subject to any disclaimer, the term of this patent is extended or adjusted under 35 U.S.C. 154(b) by 0 days.

(21) Appl. No.: 13/237,170

(22) Filed: Sep. 20, 2011

(65) Prior Publication Data

US 2012/0007001 A1   Jan. 12, 2012

Related U.S. Application Data

(63) Continuation of application No. PCT/JP2010/054405, filed on Mar. 16, 2010.

(30) Foreign Application Priority Data

Mar. 24, 2009 (JP) ................................. 2009-072850

(51) Int. Cl.
*G01N 21/64* (2006.01)
(52) U.S. Cl. .................................. 250/458.1; 250/559.3
(58) Field of Classification Search ............... 250/458.1, 250/559.3
See application file for complete search history.

(56) References Cited

U.S. PATENT DOCUMENTS

| 7,309,867 | B2 * | 12/2007 | Costa et al. | 250/458.1 |
| 7,679,785 | B2 * | 3/2010 | Ehbets et al. | 358/1.9 |
| 7,873,407 | B2 * | 1/2011 | Levenson et al. | 600/476 |
| 2011/0176723 | A1 * | 7/2011 | Ali et al. | 382/154 |

FOREIGN PATENT DOCUMENTS

| JP | 62-247232 A | 10/1987 |
| JP | 62-247332 A | 10/1987 |
| JP | 03-58729 B | 9/1991 |
| JP | 2001-137173 A | 5/2001 |
| JP | 2001-169999 A | 6/2001 |
| JP | 2003-036436 A | 2/2003 |
| JP | 2005-185452 A | 7/2005 |
| JP | 2006-175052 A | 7/2006 |
| JP | 2008-259722 A | 10/2008 |

OTHER PUBLICATIONS

International Search Report mailed May 11, 2010 in corresponding International Patent Application No. PCT/JP2010/054405.

* cited by examiner

*Primary Examiner* — David Porta
*Assistant Examiner* — Hugh H Maupin
(74) *Attorney, Agent, or Firm* — Scully, Scott, Murphy & Presser, P.C.

(57) ABSTRACT

Observation is performed with a fluorescence image having high quantitativeness by satisfactorily eliminating dependencies on distance and angle that remain in an image subjected to division. Provided is a fluoroscopy system 1 including a fluoroscopy apparatus (100); a calibration device (101) equipped with a standard specimen (30) and an observation-state setting mechanism (31), (32) that sets, in a variable manner, an observation distance D and an observation angle θ of the fluoroscopy apparatus (100) relative to the standard specimen (30); and an observation-conditions adjusting portion (10) that adjusts observation conditions on the basis of the set observation distance D and observation angle θ and a reference image $G_1$ and a fluorescence image $G_2$ acquired by capturing the standard specimen (30) with the fluoroscopy apparatus (100).

22 Claims, 12 Drawing Sheets

FLUOROSCOPY SYSTEM, FLUOROSCOPY APPARATUS, AND FLUOROSCOPY METHOD

CROSS-REFERENCE TO RELATED APPLICATIONS

This is a continuation of International Application PCT/JP2010/054405, with an international filing date of Mar. 16, 2010, which is hereby incorporated by reference herein in its entirety. This application claims the benefit of Japanese Patent Application No. 2009-072850, the content of which is incorporated herein by reference.

TECHNICAL FIELD

The present invention relates to a fluoroscopy system, a fluoroscopy apparatus, and a fluoroscopy method.

BACKGROUND ART

With a known method in the related art (for example, see Patent Literatures 1 to 3), brightness variation in a fluorescence image due to observation distance and observation angle is corrected by dividing a fluorescence image by a reflected-light image.

CITATION LIST

Patent Literature

{PTL 1} Japanese Unexamined Patent Application, Publication No. Sho 62-247232.
{PTL 2} Japanese Examined Patent Application, Publication No. Hei 3-58729.
{PTL 3} Japanese Unexamined Patent Application, Publication No. 2006-175052.

SUMMARY OF INVENTION

Technical Problem

Fluorescence and reflected light differ in terms of the dependency of the acquired brightness on observation distance and the dependency thereof on observation angle; therefore, the influences of distance and angle cannot be completely corrected by simply dividing a fluorescence image by a reflected-light image.

The present invention provides a fluoroscopy apparatus, a fluoroscopy system, and a fluoroscopy method that enable observation with a fluorescence image having high quantitativeness by satisfactorily removing dependencies on distance and angle remaining in an image that has been subjected to division.

Solution to Problem

A fluoroscopy system according to a first aspect of the present invention is a fluoroscopy system including: a fluoroscopy apparatus including an illumination portion provided with a light source that radiates illumination light and excitation light, a fluorescence imaging portion that acquires a fluorescence image by imaging fluorescence generated at a subject, a return-light imaging portion that acquires a reference image by imaging return light returning from the subject, and an image-correcting unit that corrects the fluorescence image imaged by the fluorescence imaging portion by using the reference image acquired by the return-light imaging portion; a calibration device connected to the fluoroscopy apparatus and including a standard specimen and an observation-state setting mechanism that sets, in a variable manner, an observation distance and an observation angle of the fluoroscopy apparatus relative to the standard specimen; and an observation-conditions adjusting portion that adjusts observation conditions on the basis of the observation distance and the observation angle set by the calibration device and the fluorescence image and the reference image acquired by imaging the standard specimen with the fluoroscopy apparatus, wherein the observation-conditions adjusting portion calculates exponents a to d on the basis of the observation distance and the observation angle set by the calibration device and the fluorescence image and the reference image acquired by imaging the standard specimen with the fluoroscopy apparatus and adjusts the observation conditions so that $\epsilon = |ad - bc|$ becomes a prescribed threshold $\epsilon_{max}$ or less, and wherein the image-correcting unit performs the following processing:

$$FL_{revisedrevised} = FL_{after}/RL_{after},$$

where
$FL_{revisedrevised}$ is a luminance value of the corrected fluorescence image, $$FL_{after} = A \times FL_{before}^{x},$$

$$RL_{after} = B \times RL_{before}^{y},$$

$FL_{before}$ and $RL_{before}$ are luminance values of the acquired fluorescence image and reference image,
A and B are constants, $$x = (cn - dm)/(bc - ad) \qquad (1),$$

$$y = (an - bm)/(bc - ad) \qquad (2),$$

a is an exponent obtained by applying a power approximation to a characteristic of luminance versus distance from the illumination portion to the standard specimen, for the fluorescence image obtained by the fluorescence imaging portion when excitation light of a prescribed intensity is radiated towards the standard specimen,
b is an exponent obtained by applying a power approximation to a characteristic of luminance versus cosine from the illumination portion to the standard specimen, for the fluorescence image obtained by the fluorescence imaging portion when excitation light of a prescribed intensity is radiated towards the standard specimen,
c is an exponent obtained by applying a power approximation to a characteristic of luminance versus distance from the illumination portion to the standard specimen, for the reference image obtained by the return-light imaging portion when illumination light of a prescribed intensity is radiated towards the standard specimen,
d is an exponent obtained by applying a power approximation to a characteristic of luminance versus cosine from the illumination portion to the standard specimen, for the reference image obtained by the return-light imaging portion when illumination light of a prescribed intensity is radiated towards the standard specimen, $$r_D^{|m|} \cdot r_\theta^{|n|} \leq 1 + e_{max} \qquad (3),$$

$r_D = D_{max}/D_{min},$
$r_\theta = \cos\theta_{min}/\cos\theta_{max},$
$D_{max}$ is a presumed maximum observation distance,
$D_{min}$ is a presumed minimum observation distance,
$\theta_{max}$ is a presumed maximum observation angle,
$\theta_{min}$ is a presumed minimum observation angle (where, $0° \leq \theta_{min} < \theta_{max} \leq 90°$),
m and n are arbitrary constants that satisfy Expression (3),
$e_{max}$ is $(FL_{after}/RL_{after})_{max} \div (FL_{after}/RL_{after})_{min} - 1$;

$(FL_{after}/RL_{after})_{max}$ is a maximum value within a range from the presumed minimum observation distance to the presumed maximum observation distance and within a range from the presumed minimum observation angle to the presumed maximum observation angle, $FL_{after}/RL_{after})_{min}$ is a minimum value within a range from the presumed minimum observation distance to the presumed maximum observation distance and within a range from the presumed minimum observation angle to the presumed maximum observation angle, and when $bc-ad=0$, x and y are set from arbitrary real numbers that satisfy $x:y=c:a=d:b$.

A fluoroscopy system according to a second aspect of the present invention is a fluoroscopy system including: a fluoroscopy apparatus including an illumination portion provided with a light source that radiates illumination light and excitation light, a fluorescence imaging portion that acquires a fluorescence image by imaging fluorescence generated at a subject, a return-light imaging portion that acquires a reference image by imaging return light returning from the subject, and an image-correcting unit that corrects the fluorescence image imaged by the fluorescence imaging portion by using the reference image acquired by the return-light imaging portion; a calibration device connected to the fluoroscopy apparatus and including a standard specimen and an observation-state setting mechanism that sets, in a variable manner, an observation distance and an observation angle of the fluoroscopy apparatus relative to the standard specimen; and an observation-conditions adjusting portion that adjusts observation conditions, wherein the observation-conditions adjusting portion calculates exponents a to d on the basis of the observation angle and the observation distance set by the calibration device and the fluorescence image and the reference image acquired by imaging the standard specimen with the fluoroscopy apparatus and adjusts the observation conditions so that $\epsilon=|ad-bc|$ becomes a prescribed threshold $\epsilon_{max}$ or less, and wherein the image-correcting unit performs the following processing:

$$FL_{revisedrevised}=(FL_{after}/RL_{after})^{1/x},$$

where $FL_{revisedrevised}$ is a luminance value of the corrected fluorescence image, $$FL_{after}=A \times FL_{before}^x,$$

$$RL_{after}=B \times RL_{before}^y,$$

$FL_{before}$ and $RL_{before}$ are luminance values of the acquired fluorescence image and reference image, A and B are constants, $$x:y=c:(a-m)=d:(b-n) \qquad (4),$$

a is an exponent obtained by applying a power approximation to a characteristic of luminance versus distance from the illumination portion to the standard specimen, for the fluorescence image obtained by the fluorescence imaging portion when excitation light of a prescribed intensity is radiated towards the standard specimen, b is an exponent obtained by applying a power approximation to a characteristic of luminance versus cosine from the illumination portion to the standard specimen, for the fluorescence image obtained by the fluorescence imaging portion when excitation light of a prescribed intensity is radiated towards the standard specimen, c is an exponent obtained by applying a power approximation to a characteristic of luminance versus distance from the illumination portion to the standard specimen, for the reference image obtained by the return-light imaging portion when illumination light of a prescribed intensity is radiated towards the standard specimen, d is an exponent obtained by applying a power approximation to a characteristic of luminance versus cosine from the illumination portion to the standard specimen, for the reference image obtained by the return-light imaging portion when illumination light of a prescribed intensity is radiated towards the standard specimen, $$r_D^{|m|} \cdot r_\theta^{|n|} \leq 1+e_{max} \qquad (3),$$

$r_D = D_{max}/D_{min}$,
$r_\theta = \cos\theta_{min}/\cos\theta_{max}$,
$D_{max}$ is a presumed maximum observation distance,
$D_{min}$ is a presumed minimum observation distance,
$\theta_{max}$ is a presumed maximum observation angle,
$\theta_{min}$ is a presumed minimum observation angle (where, $0° \leq \theta_{min} < \theta_{max} \leq 90°$), m and n are arbitrary constants that satisfy Expressions (3) and (4), $e_{max}$ is $(FL_{after}/RL_{after})_{max} \div (FL_{after}/RL_{after})_{min} - 1$;

$(FL_{after}/RL_{after})_{max}$ is a maximum value within a range from the presumed minimum observation distance to the presumed maximum observation distance and within a range from the presumed minimum observation angle to the presumed maximum observation angle, and $(FL_{after}/RL_{after})_{min}$ is a minimum value within a range from the presumed minimum observation distance to the presumed maximum observation distance and within a range from the presumed minimum observation angle to the presumed maximum observation angle.

A fluoroscopy apparatus according to a third aspect of the present invention is a fluoroscopy apparatus including: an illumination portion provided with a light source that radiates illumination light and excitation light, a fluorescence imaging portion that acquires a fluorescence image by imaging fluorescence generated at a subject, a return-light imaging portion that acquires a reference image by imaging return light returning from the subject, and an image-correcting unit that corrects the fluorescence image imaged by the fluorescence imaging portion using the reference image acquired by the return-light imaging portion; an attachable/detachable part that is attached/detached to change observation conditions; an identification-information input device that inputs identification information assigned to the attachable/detachable part; a storage unit that stores the identification information, exponents x and y, and the observation conditions in association with each other; and an observation-conditions adjusting portion that sets the observation conditions to the observation conditions stored in the storage unit in association with the identification information input by the identification-information input device when the attachable/detachable part is connected, wherein the image-correcting unit performs the following processing using the exponents x and y stored in the storage unit in association with the identification information input by the identification-information input device:

$$FL_{revised}=FL_{after}/RL_{after}$$

where $FL_{revised}$ is a luminance value of the corrected fluorescence image, $$FL_{after}=A \times FL_{before}^x,$$

$$RL_{after}=B \times RL_{before}^y,$$

$FL_{before}$ and $RL_{before}$ are luminance values of the acquired fluorescence image and reference image, A and B are constants, $$x=(cn-dm)/(bc-ad) \quad (1),$$

$$y=(an-bm)/(bc-ad) \quad (2),$$

a is an exponent obtained by applying a power approximation to a characteristic of luminance versus distance from the illumination portion to the subject, for the fluorescence image obtained by the fluorescence imaging portion when excitation light of a prescribed intensity is radiated towards the subject, b is an exponent obtained by applying a power approximation to a characteristic of luminance versus cosine from the illumination portion to the subject, for the fluorescence image obtained by the fluorescence imaging portion when excitation light of a prescribed intensity is radiated towards the subject, c is an exponent obtained by applying a power approximation to a characteristic of luminance versus distance from the illumination portion to the subject, for the reference image obtained by the return-light imaging portion when illumination light of a prescribed intensity is radiated towards the subject, d is an exponent obtained by applying a power approximation to a characteristic of luminance versus cosine from the illumination portion to the subject, from the reference image obtained by the return-light imaging portion when illumination light of a prescribed intensity is radiated towards the subject, $$r_D^{|m|} \cdot r_\theta^{|n|} \leq 1 + e_{max} \quad (3),$$

$r_D = D_{max}/D_{min}$,
$r_\theta = \cos\theta_{min}/\cos\theta_{max}$,
$D_{max}$ is a presumed maximum observation distance,
$D_{min}$ is a presumed minimum observation distance,
$\theta_{max}$ is a presumed maximum observation angle,
$\theta_{min}$ is a presumed minimum observation angle (where, $0° \leq \theta_{min} < \theta_{max} \leq 90°$),
m and n are arbitrary constants that satisfy Expression (3),
$e_{max}$ is $(FL_{after}/RL_{after})_{max} \div (FL_{after}/RL_{after})_{min} - 1$;
$(FL_{after}/RL_{after})_{max}$ is a maximum value within a range from the presumed minimum observation distance to the presumed maximum observation distance and within a range from the presumed minimum observation angle to the presumed maximum observation angle,
$FL_{after}/RL_{after})_{min}$ is a minimum value within a range from the presumed minimum observation distance to the presumed maximum observation distance and within a range from the presumed minimum observation angle to the presumed maximum observation angle, and when bc−ad=0, x and y are set from arbitrary real numbers that satisfy x:y=c:a=d:b.

A fluoroscopy apparatus according to a fourth aspect of the present invention is a fluoroscopy apparatus including: an illumination portion provided with a light source that radiates illumination light and excitation light, a fluorescence imaging portion that acquires a fluorescence image by imaging fluorescence generated at a subject, a return-light imaging portion that acquires a reference image by imaging return light returning from the subject, and an image-correcting unit that corrects the fluorescence image imaged by the fluorescence imaging portion using the reference image acquired by the return-light imaging portion; an attachable/detachable part that is attached/detached to change observation conditions; an identification-information input device that inputs identification information assigned to the attachable/detachable part; a storage unit that stores the identification information, exponents x and y, and the observation conditions in association with each other; and an observation-conditions adjusting portion that sets the observation conditions to the observation conditions stored in the storage unit in association with the identification information input by the identification-information input device when the attachable/detachable part is connected, wherein the image-correcting unit performs the following processing using the exponents x and y stored in the storage unit in association with the identification information input by the identification-information input device:

$$FL_{revised} = (FL_{after}/RL_{after})^{1/x},$$

where
$FL_{revised}$ is a luminance value of the corrected fluorescence image, $$FL_{after} = A \times FL_{before}^x,$$

$$RL_{after} = B \times RL_{before}^y,$$

$FL_{before}$ and $RL_{before}$ are luminance values of the acquired fluorescence image and reference image,
A and B are constants, $$x:y=c:(a-m)=d:(b-n) \quad (4),$$

a is an exponent obtained by applying a power approximation to a characteristic of luminance versus distance from the illumination portion to the subject, for the fluorescence image obtained by the fluorescence imaging portion when excitation light of a prescribed intensity is radiated towards the subject, b is an exponent obtained by applying a power approximation to a characteristic of luminance versus cosine from the illumination portion to the subject, for the fluorescence image obtained by the fluorescence imaging portion when excitation light of a prescribed intensity is radiated towards the subject, c is an exponent obtained by applying a power approximation to a characteristic of luminance versus distance from the illumination portion to the subject, for the reference image obtained by the return-light imaging portion when illumination light of a prescribed intensity is radiated towards the subject, d is an exponent obtained by applying a power approximation to a characteristic of luminance versus cosine from the illumination portion to the subject, for the reference image obtained by the return-light imaging portion when illumination light of a prescribed intensity is radiated towards the subject, $$r_D^{|m|} \cdot r_\theta^{|n|} \leq 1 + e_{max} \quad (3),$$

$r_D = D_{max}/D_{min}$,
$r_\theta = \cos\theta_{min}/\cos\theta_{max}$,
$D_{max}$ is a presumed maximum observation distance,
$D_{min}$ is a presumed minimum observation distance,
$\theta_{max}$ is a presumed maximum observation angle,
$\theta_{min}$ is a presumed minimum observation angle (where, $0° \leq \theta_{min} < \theta_{max} \leq 90°$),
m and n are arbitrary constants that satisfy Expressions (3) and (4),
$e_{max}$ is $(FL_{after}/RL_{after})_{max} \div (FL_{after}/RL_{after})_{min} - 1$;
$FL_{after}/RL_{after})_{max}$ is a maximum value within a range from the presumed minimum observation distance to the presumed maximum observation distance and within a range from the presumed minimum observation angle to the presumed maximum observation angle, and
$(FL_{after}/RL_{after})_{min}$ is a minimum value within a range from the presumed minimum observation distance to the presumed maximum observation distance and within a range from the presumed minimum observation angle to the presumed maximum observation angle.

In the third and fourth aspects described above, m=0 may be set.

In the second and fourth aspects described above, the observation-conditions adjusting portion may be a wavelength-adjusting portion that adjusts the wavelength of the illumination light.

The second and fourth aspects described above may further include an objective optical system that collects the fluorescence and the return light returning from the subject, wherein the observation-conditions adjusting portion is an adjustable diaphragm provided in the objective optical system.

In any of the aspects described above, the observation-conditions adjusting portion may be an adjustable diaphragm that adjusts a beam diameter of the illumination light and the excitation light.

A fluoroscopy method according to a fifth aspect of the present invention is a fluoroscopy method including: irradiating a standard specimen with illumination light and excitation light while varying an observation distance and an observation angle, acquiring a plurality of fluorescence images at different observation distances and/or observation angles by imaging fluorescence generated at the standard specimen, acquiring a plurality of reference images at different observation distances and/or observation angles by imaging return light returning from the standard specimen, calculating exponents a to d on the basis of the acquired plurality of fluorescence images and reference images, and adjusting observation conditions so that $\epsilon = |ad-bc|$ becomes a prescribed threshold $\epsilon_{max}$ or less; irradiating a subject with illumination light and excitation light; and performing the following correction processing on a fluorescence image acquired by imaging fluorescence generated at the subject by using a reference image acquired by imaging return light returning from the subject:

$$FL_{revised} = FL_{after}/RL_{after},$$

where $FL_{revised}$ is a luminance value of the corrected fluorescence image, $$FL_{after} = A \times FL_{before}^{x},$$

$$RL_{after} = B \times RL_{before}^{y},$$

$FL_{before}$ and $RL_{before}$ are luminance values of the acquired fluorescence image and reference image, A and B are constants, $$x = (cn-dm)/(bc-ad) \quad (1),$$

$$y = (an-bm)/(bc-ad) \quad (2),$$

a is an exponent obtained by applying a power approximation to a characteristic of luminance versus distance from the illumination portion to the standard specimen, for the fluorescence image obtained by a fluorescence imaging portion when excitation light of a prescribed intensity is radiated towards the standard specimen, b is an exponent obtained by applying a power approximation to a characteristic of luminance versus cosine from the illumination portion to the standard specimen, for the fluorescence image obtained by the fluorescence imaging portion when excitation light of a prescribed intensity is radiated towards the standard specimen, c is an exponent obtained by applying a power approximation to a characteristic of luminance versus distance from the illumination portion to the standard specimen, for the reference image obtained by a return-light imaging portion when illumination light of a prescribed intensity is radiated towards the standard specimen, d is an exponent obtained by applying a power approximation to a characteristic of luminance versus cosine from the illumination portion to the standard specimen, for the reference image obtained by the return-light imaging portion when illumination light of a prescribed intensity is radiated towards the standard specimen, $$r_D^{|m|} \cdot r_\theta^{|n|} \leq 1 + e_{max} \quad (3),$$

$r_d = D_{max}/D_{min}$,
$r_\theta = \cos\theta_{min}/\cos\theta_{max}$,
$D_{max}$ is a presumed maximum observation distance,
$D_{min}$ is a presumed minimum observation distance,
$\theta_{max}$ is a presumed maximum observation angle,
$\theta_{min}$ is a presumed minimum observation angle (where, $0° \leq \theta_{min} < \theta_{max} \leq 90°$),
m and n are arbitrary constants that satisfy Expression (3),
$e_{max}$ is $(FL_{after}/RL_{after})_{max} \div (FL_{after}/RL_{after})_{min} - 1$;
$(FL_{after}/RL_{after})_{max}$ is a maximum value within a range from the presumed minimum observation distance to the presumed maximum observation distance and within a range from the presumed minimum observation angle to the presumed maximum observation angle,
$(FL_{after}/RL_{after})_{min}$ is a minimum value within a range from the presumed minimum observation distance to the presumed maximum observation distance and within a range from the presumed minimum observation angle to the presumed maximum observation angle, and when $bc-ad=0$, x and y are set from arbitrary real numbers that satisfy $x:y=c:a=d:b$.

A fluoroscopy method according to a sixth aspect of the present invention is a fluoroscopy method including: irradiating a standard specimen with illumination light and excitation light while varying an observation distance and an observation angle, acquiring a plurality of fluorescence images at different observation distances and/or observation angles by imaging fluorescence generated at the standard specimen, acquiring a plurality of reference images at different observation distances and/or observation angles by imaging return light returning from the standard specimen, calculating exponents a to d on the basis of the acquired plurality of fluorescence images and reference images, and adjusting observation conditions so that $\epsilon = |ad-bc|$ becomes a prescribed threshold $\epsilon_{max}$ or less; irradiating a subject with illumination light and excitation light; and performing the following correction processing on a fluorescence image acquired by imaging fluorescence generated at the subject by using a reference image acquired by imaging return light returning from the subject:

$$FL_{revised} = FL_{after}/RL_{after})^{1/x},$$

where
$FL_{revised}$ is a luminance value of the corrected fluorescence image, $$FL_{after} = A \times FL_{before}^{x},$$

$$RL_{after} = B \times RL_{before}^{y},$$

$FL_{before}$ and $RL_{before}$ are luminance values of the acquired fluorescence image and reference image, A and B are constants, $$x:y=c:(a-m)=d:(b-n) \quad (4),$$

a is an exponent obtained by applying a power approximation to a characteristic of luminance versus distance from the illumination portion to the standard specimen, for the fluorescence image obtained by a fluorescence imaging portion when excitation light of a prescribed intensity is radiated towards the standard specimen, b is an exponent obtained by applying a power approximation to a characteristic of luminance versus cosine from the illumination portion to the standard specimen, for the fluorescence image obtained by the fluorescence imaging portion when excitation light of a prescribed intensity is radiated towards the standard specimen, c is an exponent obtained by applying a power approximation to a characteristic of luminance versus distance from the illumination portion to the standard specimen, for the reference image obtained by a return-light imaging portion when illumination light of a prescribed intensity is radiated towards the standard specimen, d is an exponent obtained by applying a power approximation to a characteristic of luminance versus cosine from the illumination portion to the standard specimen, for the reference image obtained by the return-light imaging portion when illumination light of a prescribed intensity is radiated towards the standard specimen, $$r_D{}^{|m|} \cdot r_\theta{}^{|n|} \leq 1 + e_{max} \qquad (3),$$

$r_D = D_{max}/D_{min}$,
$r_\theta = \cos\theta_{min}/\cos\theta_{max}$,
$D_{max}$ is a presumed maximum observation distance,
$D_{min}$ is a presumed minimum observation distance,
$\theta_{max}$ is a presumed maximum observation angle,
$\theta_{min}$ is a presumed minimum observation angle (where, $0° \leq \theta_{min} < \theta_{max} \leq 90°$),
m and n are arbitrary constants that satisfy Expressions (3) and (4),
$e_{max}$ is $(FL_{after}/RL_{after})_{max} \div (FL_{after}/RL_{after})_{min} - 1$;
$(FL_{after}/RL_{after})_{max}$ is a maximum value within a range from the presumed minimum observation distance to the presumed maximum observation distance and within a range from the presumed minimum observation angle to the presumed maximum observation angle,
$(FL_{after}/RL_{after})_{min}$ is a minimum value within a range from the presumed minimum observation distance to the presumed maximum observation distance and within a range from the presumed minimum observation angle to the presumed maximum observation angle.

DESCRIPTION OF EMBODIMENTS

A fluoroscopy system 1 according to an embodiment of the present invention will be described below with reference to the drawings.

Figure 1:
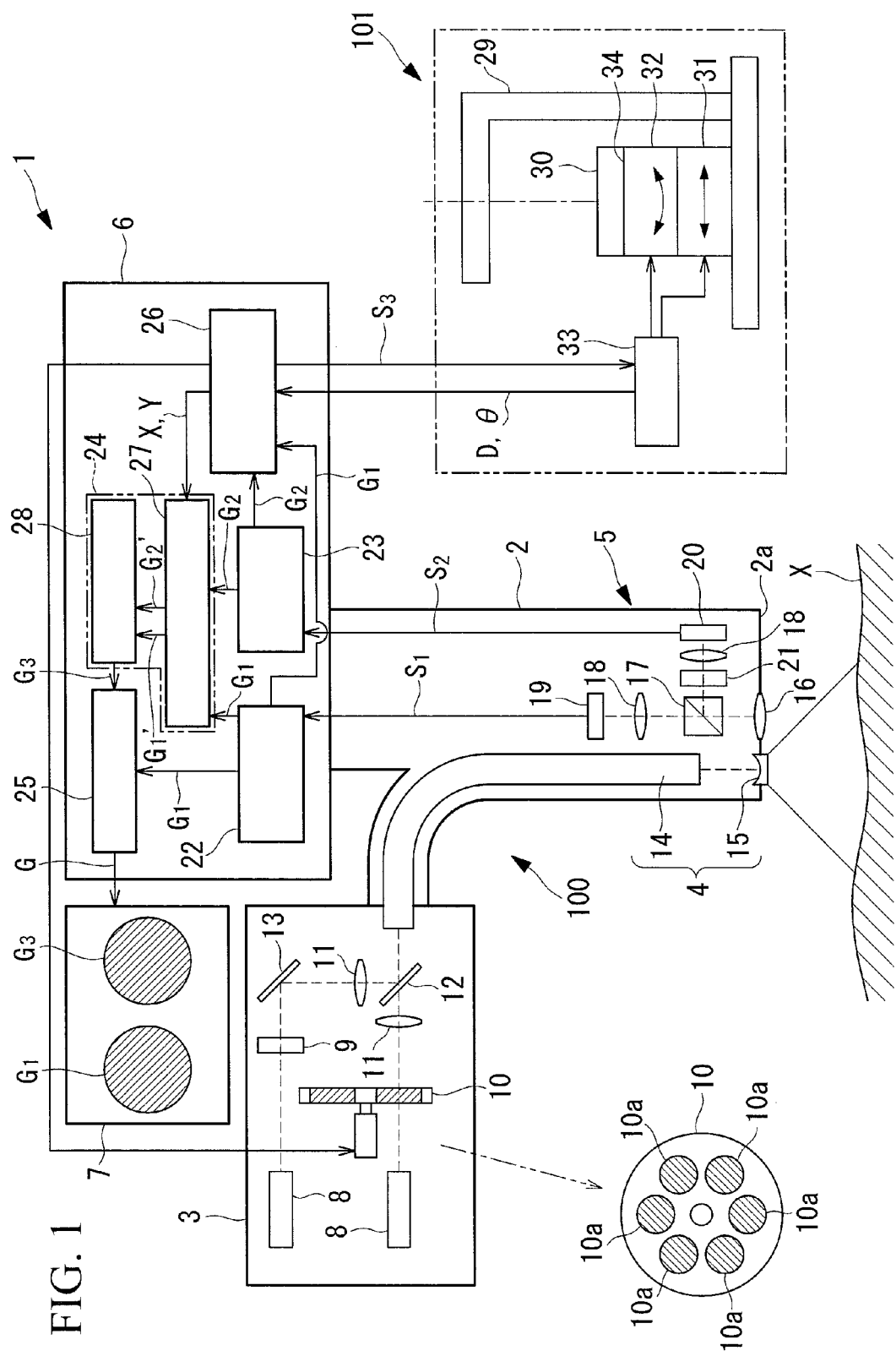
FIG. 1 is a diagram showing the overall configuration of a fluoroscopy system according to an embodiment of the present invention.

As shown in FIG. 1, the fluoroscopy system 1 according to this embodiment is equipped with a fluoroscopy apparatus 100, formed of an endoscope device, and a calibration device 101 that can be combined with the fluoroscopy apparatus 100.

The fluoroscopy apparatus 100 includes a long, thin inserted portion 2 to be inserted inside a body; a light source (illumination portion) 3; an illumination unit (illumination portion) 4 that radiates illumination light and excitation light, coming from the light source 3, towards a subject X from an end of the inserted portion 2; an image-acquisition unit 5 that is disposed at the end of the inserted portion 2 and that acquires image information of biological tissue, that is, the subject X; an image processing unit 6 that is located at the base end of the inserted portion 2 and that processes the image information acquired by the image-acquisition unit 5; and a monitor 7 that displays an image G processed by the image processing unit 6.

The light source 3 includes two xenon lamps 8; an excitation filter 9 that extracts excitation light (for example, in the wavelength band of 650 to 740 nm) from the illumination light emitted from one xenon lamp 8; a variable-wavelength filter turret (wavelength adjusting portion: observation-conditions adjusting portion) 10 that extracts the illumination light emitted from the other xenon lamp 8; coupling lenses 11 that condense the excitation light and the illumination light extracted by the excitation filter 9 and the filter turret 10; and a dichroic mirror 12 that multiplexes the excitation light and the illumination light condensed by the coupling lenses 11 onto the same optical path. Reference sign 13 in the figure is a mirror.

The illumination unit 4 includes a light-guide fiber 14 that is disposed over substantially the entire length of the inserted portion 2 in the longitudinal direction thereof and that guides the excitation light and the illumination light condensed by the coupling lenses 11, and an illumination optical system 15 that is provided at the end of the inserted portion 2, that spreads the excitation light and the illumination light guided by the light-guide fiber 14, and that irradiates the subject X opposing an end face 2a of the inserted portion 2.

The image-acquisition unit 5 includes an objective lens 16 that collects return light returning from a specific observation region of the subject X; a dichroic mirror 17 that reflects light of the excitation wavelength or higher (excitation light and fluorescence) in the return light collected by the objective lens 16 and transmits illumination light with wavelengths shorter than the excitation wavelength; two focusing lenses (image-acquisition optical systems) 18 that respectively focus the illumination light transmitted through the dichroic mirror 17 and the fluorescence reflected by the dichroic mirror 17; and two image-capturing devices 19 and 20, such as CCDs, that acquire images of the fluorescence and the illumination light focused by the focusing lenses 18. Reference sign 21 in the figure is an excitation light cut filter that blocks excitation light in the light reflected by the dichroic mirror 17.

The image-processing unit 6 includes a reference-image generating unit 22 that generates a reference image $G_1$ from reference image information $S_1$ obtained by the image capturing device 19; a fluorescence-image generating unit 23 that generates a fluorescence image $G_2$ from fluorescence image information $S_2$ obtained by the image capturing device 20; an image-correcting unit 24 that generates a corrected fluorescence image $G_3$ on the basis of the reference image $G_1$ and the fluorescence image $G_2$ generated by the reference-image generating unit 22 and the fluorescence-image generating unit 23; and an image-combining unit 25 that combines the corrected fluorescence image $G_3$ generated in the image-correcting unit 24 with the reference image $G_1$ generated in the reference-image generating unit 22 to generate an image G.

Here, the fluorescence image $G_2$ may be, for example, a fluorescence image from the fluorochrome Cy7. In particular, if a tumor-specific fluorescent agent, for example, a fluorescent agent formed by causing Cy7 to bind to an antibody to the cancer-specific molecule CEA (Anti-CEA antibody), is administered to the subject X in advance, it is possible to obtain a tumor-specific fluorescence image $G_2$. An image based on, for example, return light due to the illumination light being reflected at the surface of the subject X and return light due to scattering inside the subject X may be used as the reference image $G_1$.

The image-processing unit 6 further includes a dependency-constant determining section 26 that calculates exponents x and y, described later, on the basis of distance and angle information sent from the calibration device 101, described later, the reference image $G_1$ sent from the reference-image generating unit 22, and the fluorescence image $G_2$ sent from the fluorescence-image generating unit 23.

The dependency-constant determining section 26 switches the wavelength of the illumination light extracted by operating the filter turret 10 and outputs a startup signal $S_3$ to the calibration device 101 so as to calculate exponents a to d, described later, at each illumination light wavelength. Then, the dependency constant determining section 26 is configured to determine the illumination light wavelength that minimizes $\epsilon=|ad-bc|$, sets the filter turret 10 so that a filter 10a of that wavelength is disposed in the optical path, and selects the exponents x and y on the basis of the exponents a to d at that time. The dependency-constant determining section 26 and the filter turret 10 constitute an observation-conditions adjusting portion.

The method of calculating the exponents a to d in the dependency-constant determining section 26 will be described here.

Specifically, while varying distance D from the illumination unit 4 to the subject X, the average values of the luminance values in a predetermined region in the fluorescence image $G_2$ and the reference image $G_1$ obtained by irradiating the subject X with the excitation light and the illumination light from the illumination unit 4 are plotted versus distance D. Thus, exponents a and c that show the dependency with respect to observation distance D are obtained by regression of the obtained distance characteristic to a power approximation, that is, power functions $D^a$ and $D^c$.

Similarly, for the exponents b and d for the observation angle θ, while varying angle θ between the subject X and the optical axis of the illumination unit 4, the average values of the luminance values in a predetermined region in the fluorescence image $G_2$ and the reference image $G_1$ obtained by irradiating the subject X with the excitation light and the illumination light from the illumination unit 4 are plotted versus the cosine of the angle, cos θ. Thus, exponents b and d that indicate the dependency with respect to observation angle θ are obtained by regression of the obtained cosine characteristic to a power approximation, that is, power functions $\cos^b\theta$ and $\cos^d\theta$.

Next, the method of calculating the exponents x and y in the dependency-constant determining section 26 will be described.

Generally, the fluorescence image $G_2$ and the reference image $G_1$ show the following kind of dependencies with respect to the observation distance D and the observation angle θ:

$$FL_{before} \propto D^a \cos^b\theta, RL_{before} \propto D^c \cos^d\theta,$$

and dividing these without modification gives $$FL_{before}/RL_{before} \propto D^{a-c} \cos^{b-d}\theta,$$

where the observation distance D can be taken as, for example, the distance from the end of the inserted portion 2 to the surface of the subject X, and the observation angle θ can be taken as, for example, the angle between the normal to the surface of the subject X and the optical axis of the objective lens 16 (or the longitudinal axis direction of the inserted portion 2).

Thus, raising the luminance values of the fluorescence image $G_2$ and the reference image $G_1$ to the power of the exponents x and y, respectively, yields $$FL_{before}^x/RL_{before}^y \propto D^{ax-cy} \cos^{bx-dy}\theta.$$

Therefore, the exponents x and y are set so that, with m=ax−cy and n=bx−dy, m and n take permissible limits.

In other words, $$x=(cn-dm)/(bc-ad) \quad (1)$$

$$y=(an-bm)/(bc-ad) \quad (2)$$

and when the denominator bc−ad=0, the exponents x and y are set so that x:y=c:a=d:b.

For a presumed maximum observation distance $D_{max}$ and minimum observation distance $D_{min}$ and a presumed maximum observation angle $\theta_{max}$ and minimum observation angle $\theta_{min}$ ($0° \theta_{min} < \theta_{max} \leq 90°$), their respective ratios $r_D$ and $r_\theta$ are $$r_D = D_{max}/D_{min}, r_\theta = \cos\theta_{min}/\cos\theta_{max}$$

and by using a maximum permissible error ratio $e_{max}$ in the corrected fluorescence image, m and n are selected so that $$r_D^{|m|} \cdot r_\theta^{|n|} \leq 1 + e_{max}. \quad (3)$$

Here, the range of the presumed observation distance D can be determined, for example, from the depth of field of the objective lens 16, and the range of the presumed observation angle θ can be determined from, for example, the angular field of view of the objective lens 16.

$e_{max}$ is given by $$FL_{after}/RL_{after})_{max} \div (FL_{after}/RL_{after})_{min} = 1 + e_{max}.$$

Therefore, the maximum permissible error ratio $e_{max}$ should be set first in advance, then m and n should be set so as to satisfy Expression (3), and x and y should be set based on the set m and n so as to satisfy Expression (1) and Expression (2).

The image-combining unit 25 is configured to synthesize the image G so that, for example, the reference image $G_1$ and the corrected fluorescence image $G_3$ are simultaneously displayed side-by-side on the monitor 7 and outputs the image G to the monitor 7.

The image-correcting unit 24 includes a preprocessing unit 27 that subjects the reference image $G_1$ generated by the reference-image generating unit 22 and the fluorescence image $G_2$ generated by the fluorescence-image generating unit 23 to preprocessing, and a division processing unit 28 that divides a fluorescence image $G_2'$ subjected to preprocessing in the preprocessing unit 27 by a reference image $G_1'$ subjected to preprocessing therein.

The preprocessing unit 27 is configured to realize the following image processing method.

$$FL_{after} = A \times FL_{before}^{x} \quad (5)$$

$$RL_{after} = B \times RL_{before}^{y} \quad (6)$$

where $FL_{before}$, $RL_{before}$ luminance values of the acquired fluorescence image $G_2$ and reference image $G_1$, $FL_{after}$, $RL_{after}$ luminance values of the preprocessed fluorescence image $G_2'$ and reference image $G_1'$, and A, B: constants.

In the division processing unit 28, the following division processing is performed using the luminance value $FL_{after}$ of the fluorescence image $G_2'$ and the luminance value $RL_{after}$ of the reference image $G_1'$, which have been subjected to the above preprocessing at each pixel, to obtain a luminance value $FL_{revised}$ of the corrected fluorescence image $G_3$:

$$FL_{revised} = FL_{after}/RL_{after}.$$

In this way, by mounting the fluoroscopy apparatus 100 to the calibration device 101 prior to fluoroscopy, more accurate exponents a to d can be calculated in the fluoroscopy apparatus 100 by operating the filter turret 10 on the basis of an image captured using the standard specimen 30, and it is possible to set observation conditions so that ε becomes a threshold $ε_{max}$ or less. Accordingly, it is possible to set appropriate exponents x and y that suitably reduce dependencies on observation distance D and observation angle θ, regardless of individual differences in fluoroscopy apparatuses 100 or individual differences in attachable/detachable parts, when such parts are used.

That is to say, during fluoroscopy, when the subject X is irradiated with excitation light from the illumination unit 4, a fluorescent substance present in the subject X is excited, and fluorescence is produced. The fluorescence produced is imaged by the image capturing device 20, and a fluorescence image $G_2$ is acquired. On the other hand, when the subject X is irradiated with illumination light from the illumination unit 4, the return light that returns upon being reflected, etc. at the surface of the subject X is imaged by the image capturing device 19, and a reference image $G_1$ is acquired. The acquired fluorescence image $G_2$ is corrected at the image-correcting unit 24 by using the reference image $G_1$.

Here, for the luminance value $FL_{before}$ of each pixel in the acquired fluorescence image $G_2$ and the luminance value $RL_{before}$ of the reference image $G_1$, $FL_{before} \propto D^a \cos^b θ$ and $RL_{before} \propto D^c \cos^d θ$, respectively, showing different dependencies on the observation distance D and angle θ. Therefore, in considering reduction of these dependencies by raising the luminance value $FL_{before}$ to a power of some exponent x and by raising the luminance value $RL_{before}$ to a power of some exponent y, it is possible to obtain a fluorescence image $G_2$ in which variations due to the observation conditions are suppressed and in which the dependencies on the observation distance D and the observation angle θ can be kept within a range of the maximum permissible error rate by using the exponents x and y, which are calculated from Expressions (1) and (2) by using the constants m and n that satisfy exponents a to d as calculated above and Expression (3), which allows fluoroscopy with high quantitativeness to be performed.

Figure 2:
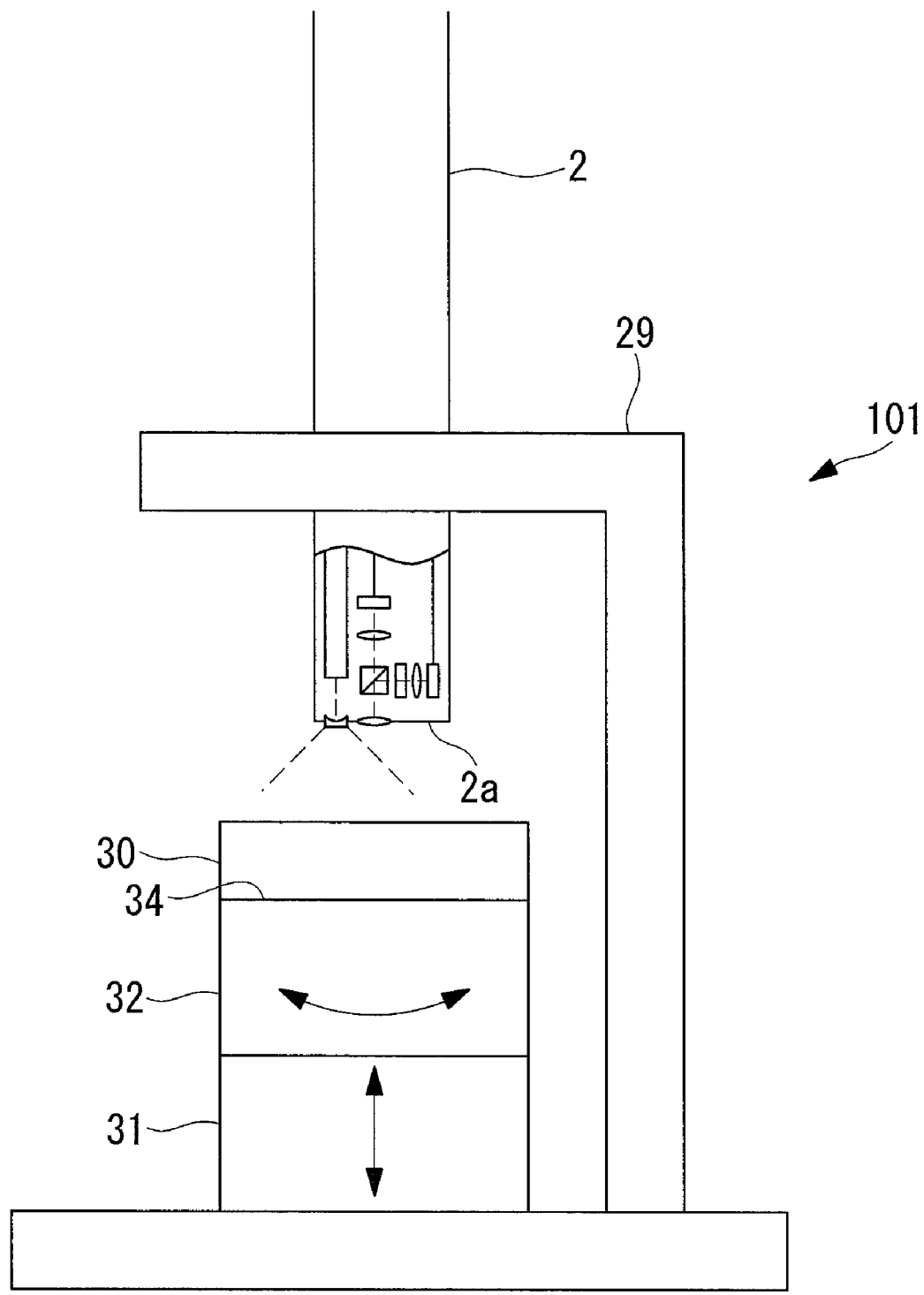
FIG. 2 is a diagram showing a calibration device of the fluoroscopy system in FIG. 1.

As shown in FIG. 2, the calibration device 101 includes a holder 29 that secures the inserted portion 2; a standard specimen 30 that can be made to oppose the end face 2a of the inserted portion 2 secured in the holder 29 so as to be separated therefrom by the observation distance; a translation stage 31 that varies the observation distance D between the end face 2a of the inserted portion 2 and the standard specimen 30; a tilt stage 32 that varies the angle (observation angle) of the surface of the standard specimen 30 relative to the optical axis of the objective lens 16; and a controller 33 that controls the stages 31 and 32.

Here, the method of setting the exponents x and y with the dependency-constant determining section 26 will be described with reference to FIGS. 3 and 4.

Figure 3:
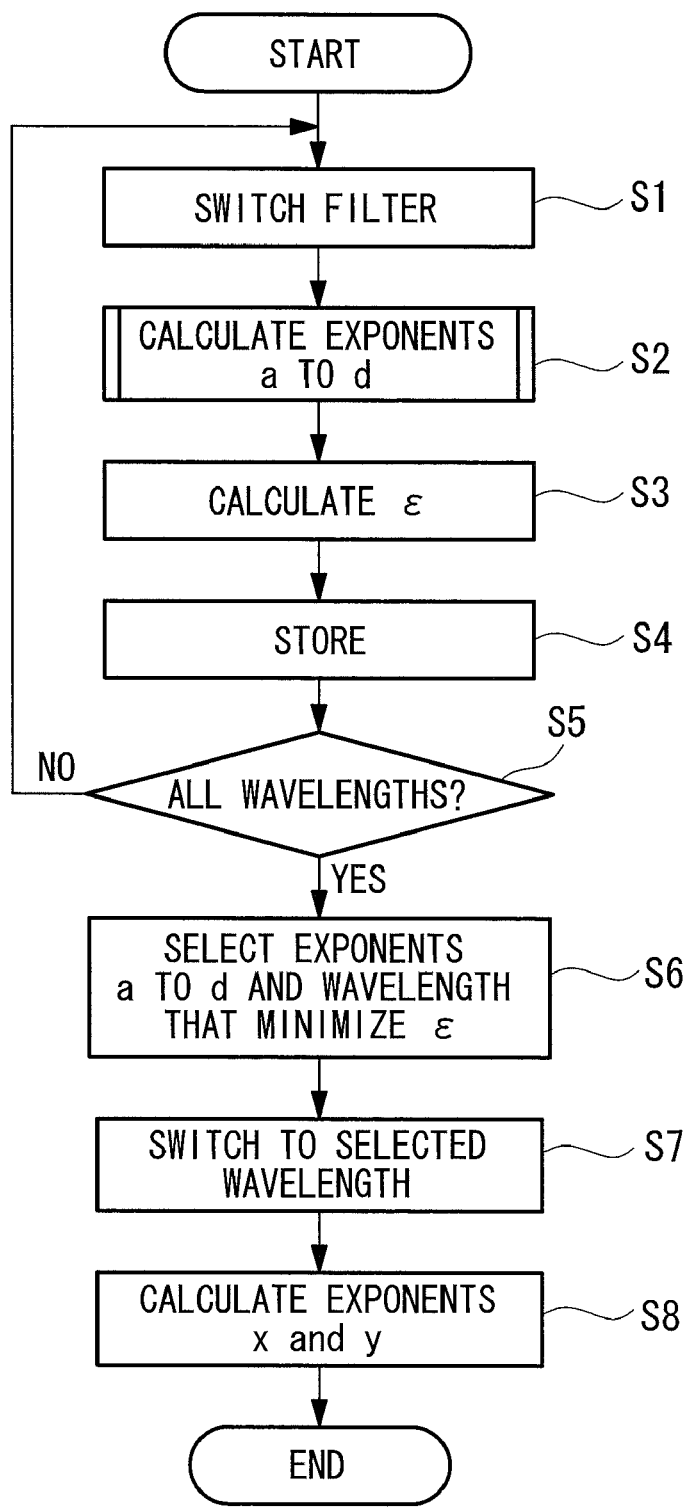
FIG. 3 is a flowchart showing a method of setting exponents x and y with a dependency-constant determining section of the fluoroscopy system in FIG. 1.

As shown in FIG. 3, the dependency-constant determining section 26 first changes the filter 10a disposed in the optical path by operating the filter turret 10 (step S1). Then, the dependency-constant determining section 26 executes step S2 of calculating the exponents a to d.

Figure 4:
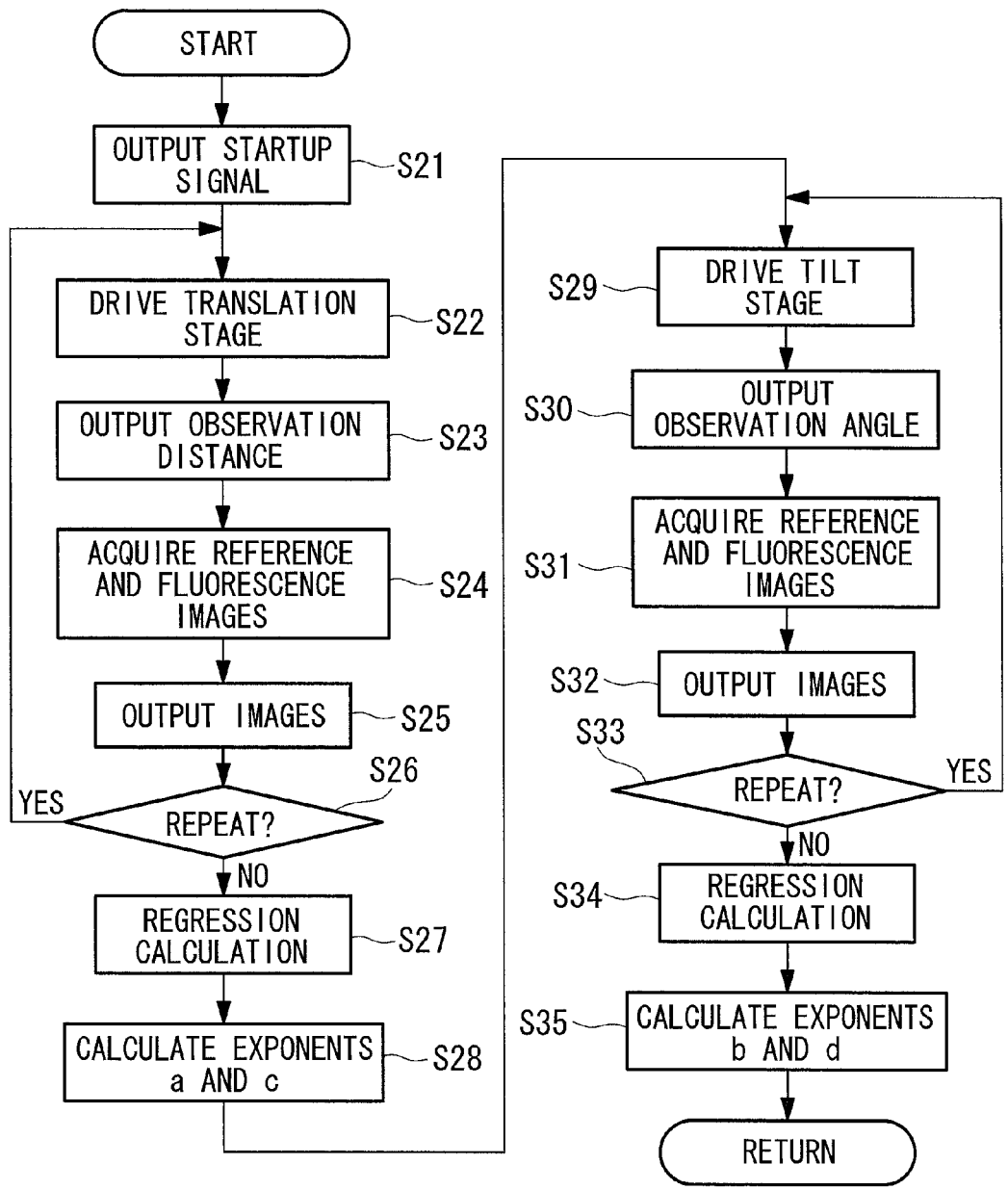
FIG. 4 is a flowchart for explaining a subroutine for calculating exponents a to d in the flowchart in FIG. 3.

In the step S2 of calculating the exponents a to d, as shown in FIG. 4, the startup signal $S_3$ is output from the dependency-constant determining section 26 to the controller 33 (step S21), and the controller 33, upon receiving the startup signal $S_3$ from the dependency-constant determining section 26, drives the individual stages 31 and 32.

First, the controller 33 drives the translation stage 31 so that the end face 2a of the inserted portion 2 is at an observation starting distance relative to the surface of the standard specimen 30 (step S22) and outputs the observation distance D at this time to the dependency-constant determining section 26 in the fluoroscopy apparatus 100 (step S23). In this state, the standard specimen 30 is irradiated with the illumination light and the excitation light from the illumination unit 4, and the return light and fluorescence are imaged (step S24). The luminance value of the fluorescence image $G_2$ generated in the fluorescence-image generating unit 21 and the luminance value of the reference image $G_1$ generated in the reference-image generating unit 20 are sent to the dependency-constant determining section 26 (step S25).

Then, the controller 33 repeats the above steps S22 to S25 multiple times for a predetermined number of times (step S26). Accordingly, the standard specimen 30 is moved so that the distance between the end face 2a of the inserted portion 2 and the surface of the standard specimen 30 takes a plurality of observation distances D, and the observation distance D is output to the dependency-constant determining section 26 each time. The luminance value of the fluorescence image $G_2$ and the luminance value of the reference image $G_1$ obtained at each observation distance D are output from the fluorescence-image generating unit 23 and the reference-image generating unit 22 to the dependency-constant determining section 26.

Accordingly, a dataset including the plurality of observation distances D as well as the luminance values of the fluorescence image $G_2$ and the reference image $G_1$ associated with the plurality of observation distances D is recorded in the dependency-constant determining section 26. Then, once a predetermined number of datasets have been collected, as described above, regression to a power function is performed (step S27), and the exponents a and c indicating the dependency with respect to the observation distance D are calculated (step S28).

Next, the controller 33 drives the translation stage 31 and the tilt stage 32 so that the end face 2a of the inserted portion 2 is at an observation starting distance and angle relative to the surface of the standard specimen 30 (step S29), and the observation angle θ at this time is output to the dependency-constant determining section 26 in the fluoroscopy apparatus 100 (step S30). In this state, the standard specimen 30 is irradiated with the illumination light and the excitation light from the illumination unit 4, and the return light and fluorescence are imaged (step S31). The luminance value of the fluorescence image $G_2$ generated in the fluorescence-image generating unit 23 and the luminance value of the reference image $G_1$ generated in the reference-image generating unit 22 are sent to the dependency-constant determining section 26 (step S32).

Then, the controller 33 repeats the above steps S29 to S32 multiple times for a predetermined number of times (step S33). Accordingly, the standard specimen 30 is moved so that the angle between the end face 2a of the inserted portion 2 and the surface of the standard specimen 30 takes a plurality of observation angles θ, and the observation angle θ is output to the dependency-constant determining section 26 each time. The luminance value of the fluorescence image $G_2$ and the luminance value of the reference image $G_1$ obtained at each observation angle θ are output from the fluorescence-image generating unit 23 and the reference-image generating unit 22 to the dependency-constant determining section 26. Thus, datasets including the plurality of observation angles θ and the luminance values of the fluorescence image $G_2$ and the reference image $G_1$ associated with the plurality of observation angles θ are recorded in the dependency-constant determining section 26, and once a predetermined number of datasets have been collected, as described above, regression to a power function is performed (step S34), and the exponents b and d indicating the dependency with respect to the observation angle θ are calculated (step S35). This completes the step S2 of calculating the exponents a to d.

Next, the dependency-constant determining section calculates $\epsilon=|ad-bc|$ (step S3), stores $\epsilon$, a to d, and the wavelength of the illumination light in association with each other (step S4), and determines whether the exponents a to d have been calculated for all required wavelengths (step S5). If the exponents a to d have not been calculated for all required wavelengths, the process returns to step S1, where the wavelength of the illumination light is switched, and step S2 to step S5 are repeated. On the other hand, if the exponents a to d have been calculated for all required wavelengths, $\epsilon$ is compared, and the illumination light wavelength and the exponents a to d that produce the minimum value are determined (step S6).

Then, the dependency-constant determining section 26 sets the filter turret 10 so that the determined illumination light wavelength is radiated (step S7). Also, the dependency-constant determining section 26 calculates the exponents x and y for correcting the variation in luminance using the exponents a to d obtained as described above and the constants m and n set on the basis of the maximum permissible error ratio $e_{max}$ which is set in advance (step S8).

Here, if it can be assumed that m=n=0 is tentatively set, the maximum permissible error ratio $e_{max}$ is not restricted and can be set to a value close to 0. In other words, the error can be reduced to a minimum.

On the other hand, for m=ax−cy and n=bx−dy, when the constants m and n are set to m=n=0, no solution other than x=y=0 exists, and therefore, such a setting is impossible. However, assuming $|ad-bc|=\epsilon$, if it is possible to set the illumination light wavelength so as to obtain the dependency with respect to observation distance D or the dependency with respect to observation angle θ that yields $\epsilon=0$, for m=ax−cy and n=bx−dy, even if the constants m and n are set to m=n=0, it is possible to set the exponents x and y so that x:y=c:a=d:b.

Therefore, it is preferable that the illumination light wavelength be set so that $\epsilon=0$, or to a value as close as possible to 0. By doing so, the dependencies with respect to both the observation distance D and the observation angle θ of the fluorescence image $G_3$ after correction can be substantially eliminated, the error can be made approximately zero, and the quantitativeness of the fluorescence image $G_3$ can be increased as much as possible.

From the above discussion, by selecting the illumination light wavelength that yields dependencies with respect to the observation distance and observation angle so that $\epsilon$ takes the minimum value, that is, a value as close to 0 as possible, it is possible to reduce the error to a minimum. In other words, even when the maximum permissible error ratio $e_{max}$ is set to the smallest possible value, there are constants m and n that satisfy Expression (3), and it is possible to set the exponents x and y on the basis of the constants m and n.

For example, when applied to an endoscope, serving as the fluoroscopy apparatus 100, even though there are different kinds, such as rigid scopes and flexible scopes, or those for different observation sites, such as upper digestive organ endoscopes and lower digestive organ endoscopes, because it is possible to set the illumination light wavelength so that the respective $\epsilon$'s are minimized, it is possible to set appropriate exponents x and y for correction according to each type. Even when a single type of fluoroscopy apparatus 100 is assumed, it is possible to set the illumination light wavelength so that $\epsilon$ is minimized for individual apparatuses, regardless of individual differences, and appropriate exponents x and y corresponding to each apparatus can be set.

With the fluoroscopy system 1 according to this embodiment, configured in this way, the dependencies with respect to the observation distance D and observation angle θ contained in the fluorescence image $G_2$ and the reference image $G_1$, which show different dependencies from each other, can be sufficiently reduced within the permissible range. Therefore, an advantage is afforded in that the corrected fluorescence image $G_3$ having a high level of quantitativeness is obtained, which allows observation with superior precision.

In this embodiment, the reference image $G_1$ and the fluorescence image $G_2$ acquired by the image-capturing devices 19 and 20 contain noise due to dark currents or read-out of the image capturing devices 19 and 20. When performing the division processing, if there is a pixel with a luminance value of zero in the reference image $G_1$, the division result becomes infinitely large, and correction cannot be carried out correctly.

Thus, an offset for eliminating the noise components due to dark currents or read-out may be applied to the fluorescence image $G_2$ in the preprocessing unit 27, and in view of eliminating the noise components due to dark currents or read-out, an offset may be applied to the reference image $G_1$ so that the luminance values of all pixels do not become zero.

In this embodiment, the illumination light wavelength that allows the exponents x and y to be set so that $\epsilon$ is minimized is selected; instead of this, however, it is possible to provide a prescribed threshold $\epsilon_{max}$ and to select the illumination light wavelength that allows the exponents x and y to be set so that $\epsilon \leq \epsilon_{max}$.

As the standard specimen 30 in this embodiment, a phantom having the same scattering and absorption properties as the body to be observed may be used, or excised tissue from a human or animal (pig, mouse, etc.) may be used.

Figure 5:
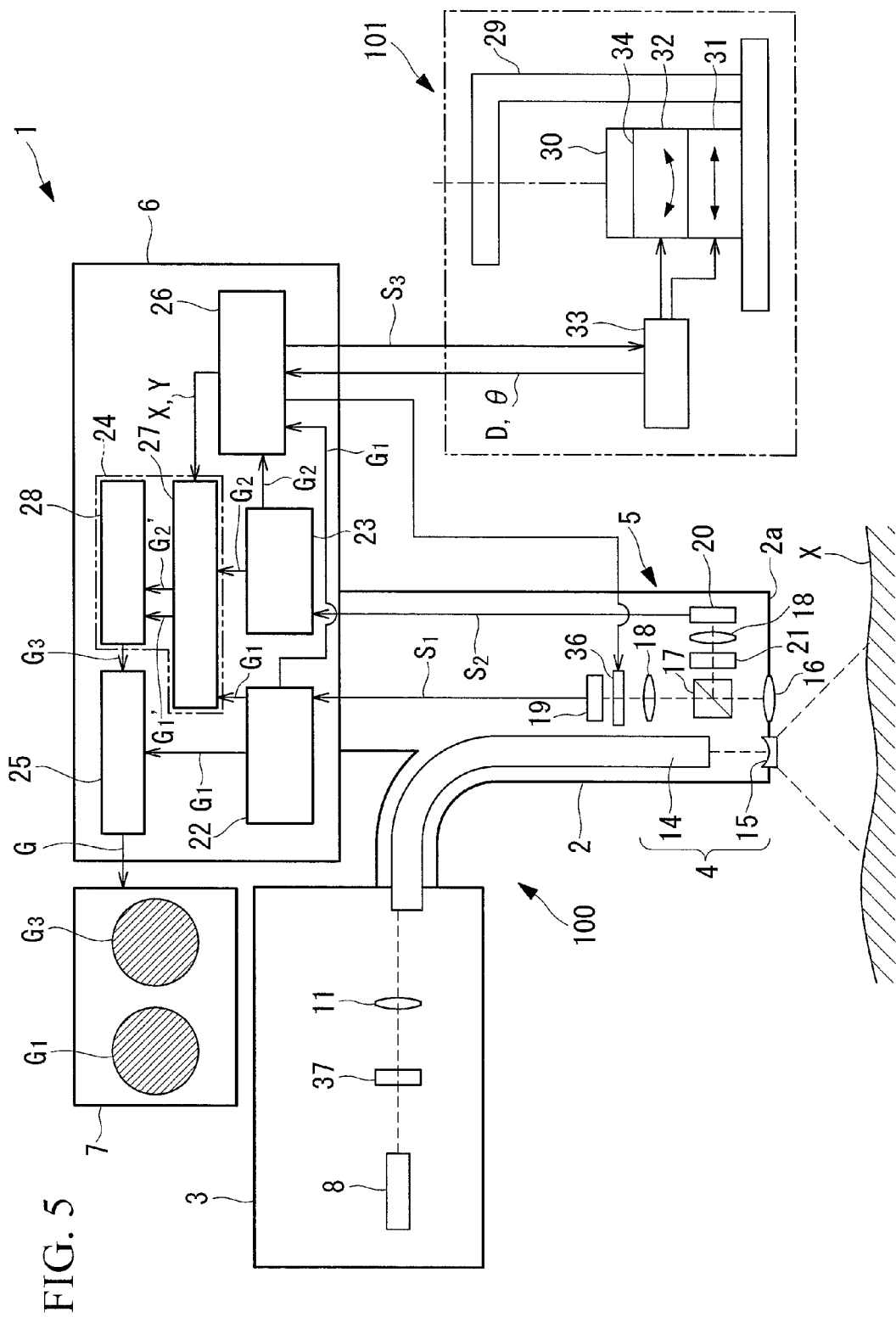
FIG. 5 is a diagram showing the overall configuration of a first modification of the fluoroscopy system in FIG. 1.

In this embodiment, although the filter turret 10, which is the wavelength-adjusting portion, is illustrated as an example of the observation-condition adjusting portion, any other means, such as a sliding-type switchable filter or an acousto-optic device, may be employed as the wavelength-adjusting portion. Instead of the filter turret 10, as shown in FIG. 5, it is possible to optimize the exponents a to d also by providing an adjustable diaphragm 36 behind the objective lens 16 to adjust the aperture of the objective lens 16. Reference sign 37 in the figure is a filter that transmits the wavelength bands of the illumination light and the excitation light.

The light that is observed is not only light reflected at the surface of the subject X, but also includes a large amount of light that returns upon being scattered inside the subject X. If the aperture of the objective lens 16 is large, a large amount of light that undergoes multiple scattering and propagates from locations distant from the optical axis can also be taken in. That is, as the aperture becomes larger, the contribution of light returning from inside the subject X increases. The ratio of light reflected at the surface of the subject X and return light from the interior is related with the dependencies with respect to the observation distance D and the observation angle θ, and therefore, the exponents a to d can be adjusted by adjusting the aperture.

Figure 6:
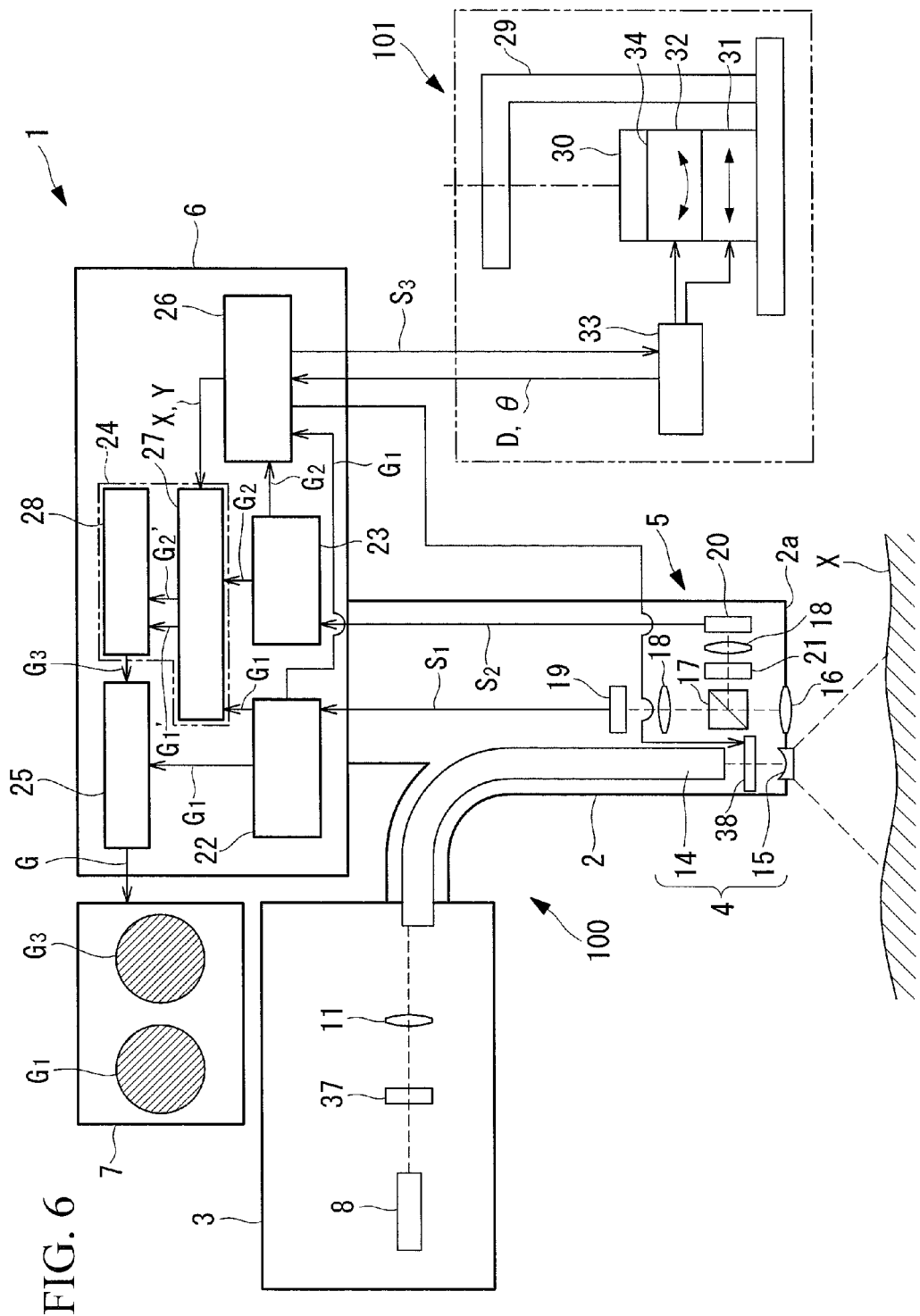
FIG. 6 is a diagram showing the overall configuration of a second modification of the fluoroscopy system in FIG. 1.

As shown in FIG. 6, an adjustable diaphragm 38 may be provided in the illumination unit 4. For example, when the aperture is a point, the illuminance at the subject X is inversely proportional to the square of the distance; however, when it is not a point, it departs from an inverse square relationship.

Figure 7:
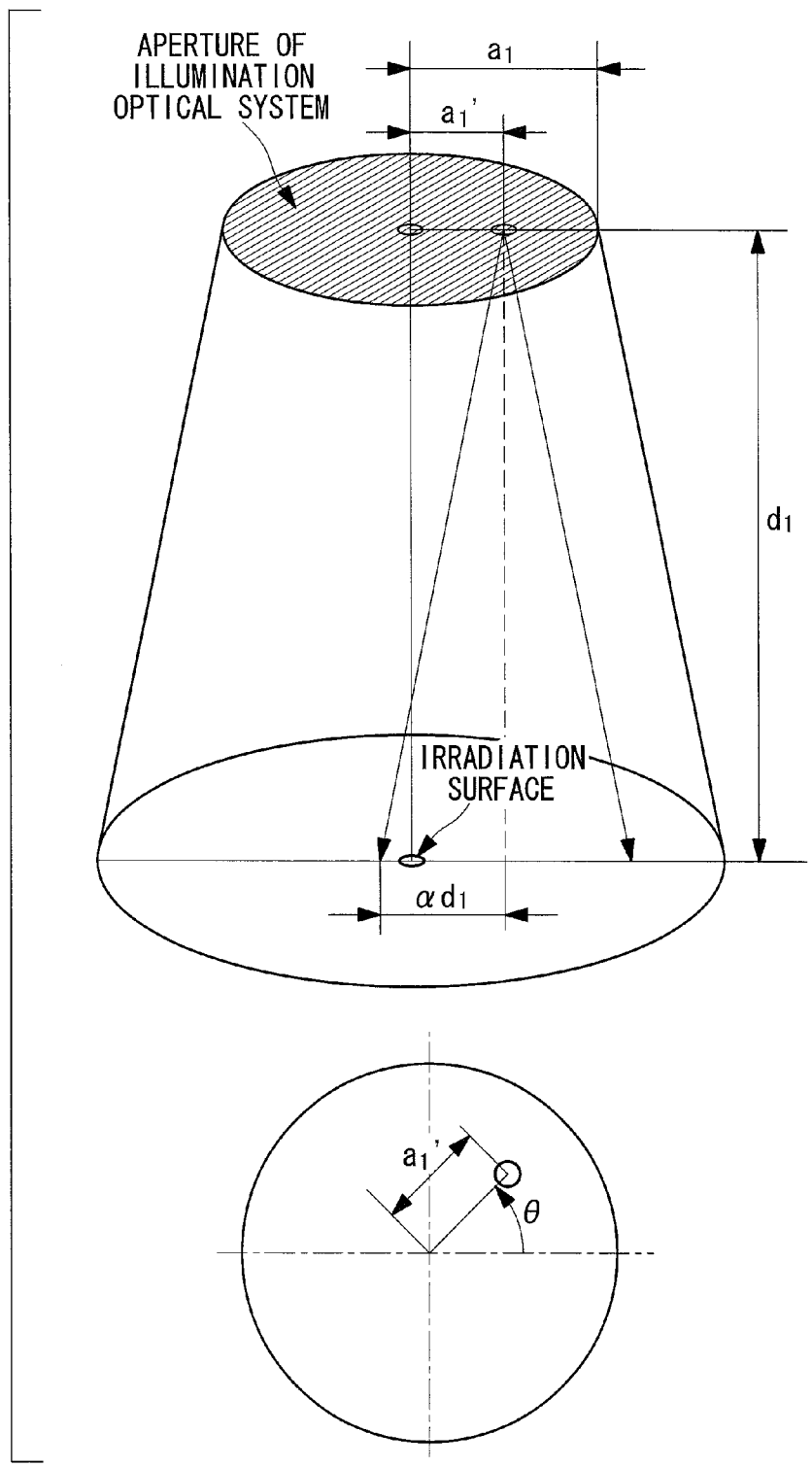
FIG. 7 is a diagram for explaining the relationship between distance and illuminance on an irradiation surface on a subject when an aperture has a limited size.

Thus, as an example, the illumination light has a Gaussian distribution centered on the optical axis, and the relationship between distance and the illuminance at the illumination surface on the subject X when the aperture has a finite size is taken into account. As shown in FIG. 7, the change in distance and illuminance at the illumination surface on the subject X separated by distance $d_1$ from the aperture of the illumination optical system 15 on the optical axis of the illumination light should be considered. Assume an aperture radius $a_1$ and distance $d_1$. What is shown here is the illuminance when a beam of light separated from the optical axis by distance $a_1'$ to $a_1'+da_1'$ at the aperture plane of the illumination optical system and emerging over a range of angles θ to θ+dθ reaches the illumination surface. The angle θ is defined as in the diagram at the bottom of FIG. 7 (a view of the aperture of the illumination optical system from below). The two one-dot chain lines intersect the optical axis of the illumination optical system and are mutually orthogonal straight lines. In terms of a constant α that is proportional to the divergence of the illumination light and the total intensity E of the illumination light, the illuminance at the illumination surface is as follows.

$$\text{illuminance} = \frac{E}{\pi a_1^2} \cdot \frac{\beta}{\pi a_1^2 d_1^2} \cdot \exp\left(-\frac{\beta}{\alpha^2 d_1^2} a_1'^2\right) da_1' \cdot a_1' d\theta \quad \text{\{Formula 1\}}$$

Here, β is a constant (a positive real number) that is related to the Gaussian half-width. (As β increases, the half-width decreases.) Therefore, the total illuminance, which is the sum of the illuminances of light emerging from all points in the aperture reaching the illumination surface, is given as follows:

$$\text{total illuminance} = \int_0^{2\pi\alpha} \int_0^E \frac{E}{\pi a_1^2} \cdot \frac{1}{d_1} \exp\left(\frac{-\beta}{\alpha^2 d_1^2} a_1'^2\right) da_1' \cdot a_1' d\theta \quad \text{\{Formula 2\}}$$

$$= \frac{E}{\pi a_1^2}\left(1 - \exp\left(-\frac{\beta}{\alpha^2 d_1^2} a_1^2\right)\right)$$

Here, when the exponents of the exponential function are approximated up to the fourth-power term, the total illuminance is given by the following:

$$\text{total illuminance} \cong \frac{\beta E}{\pi \alpha^2}\left(\frac{1}{d_1^2} - \frac{a_1^2 \beta}{2\alpha^2} \cdot \frac{1}{d_1^4}\right) \quad \text{\{Formula 3\}}$$

According to Formula 3, as the aperture becomes larger, the contribution of the term that is inversely proportional to the fourth power of the distance $d_1$ becomes larger, and the total illuminance departs from being inversely proportional to the square of the distance. Although a simple power function is not applicable in this case, by obtaining an approximation curve by the least squares method etc., it is possible to determine the approximate value.

Figure 8A:
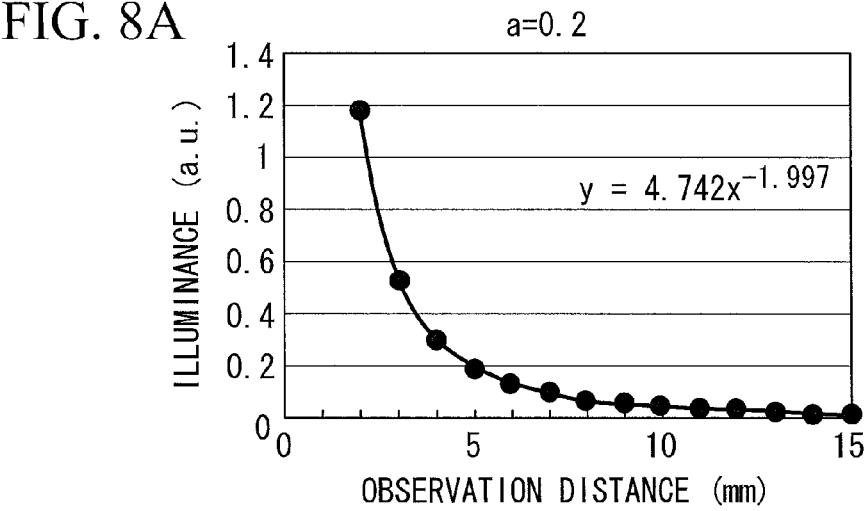
FIG. 8A is a diagram showing a graph in which the illuminance versus observation distance characteristic, obtained under prescribed conditions while varying the aperture diameter in FIG. 7, is subjected to a power approximation.
Figure 8B:
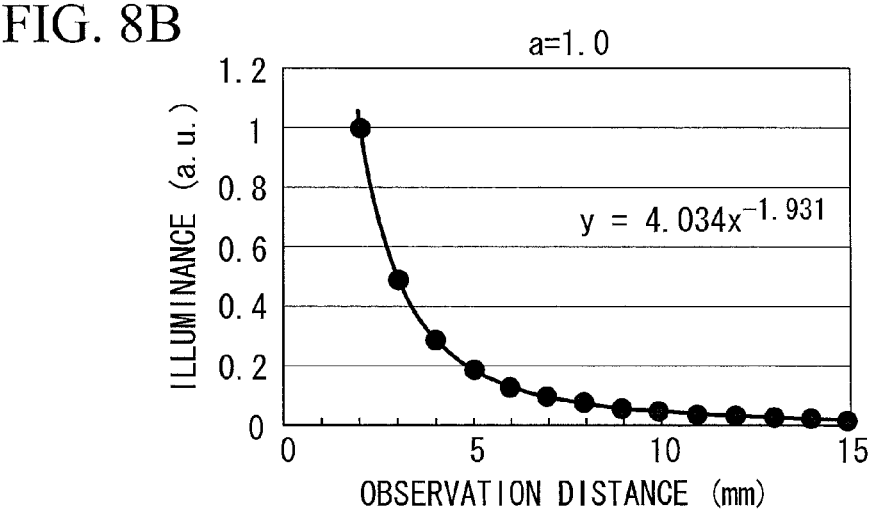
FIG. 8B is a diagram showing a graph in which the illuminance versus observation distance characteristic, obtained under prescribed conditions while varying the aperture diameter in FIG. 7, is subjected to a power approximation.
Figure 8C:
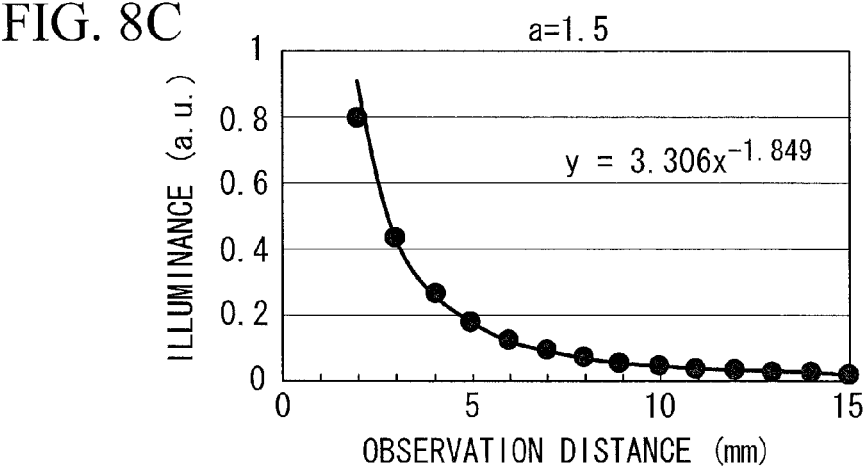
FIG. 8C is a diagram showing a graph in which the illuminance versus observation distance characteristic, obtained under prescribed conditions while varying the aperture diameter in FIG. 7, is subjected to a power approximation.

For example, with E=10, α=1, and β=1.5, when the regression curves at observation distances 2 to 15 are calculated for $a_1$=0.2, 1, and 1.5, as shown in FIGS. 8A to 8C, approximations can be made with functions that are proportional to the −1.997th power, the −1.931th power, and the −1.849th power of the distance.

Accordingly, it is possible to perform fluoroscopy with even higher quantitativeness.

Figure 9:
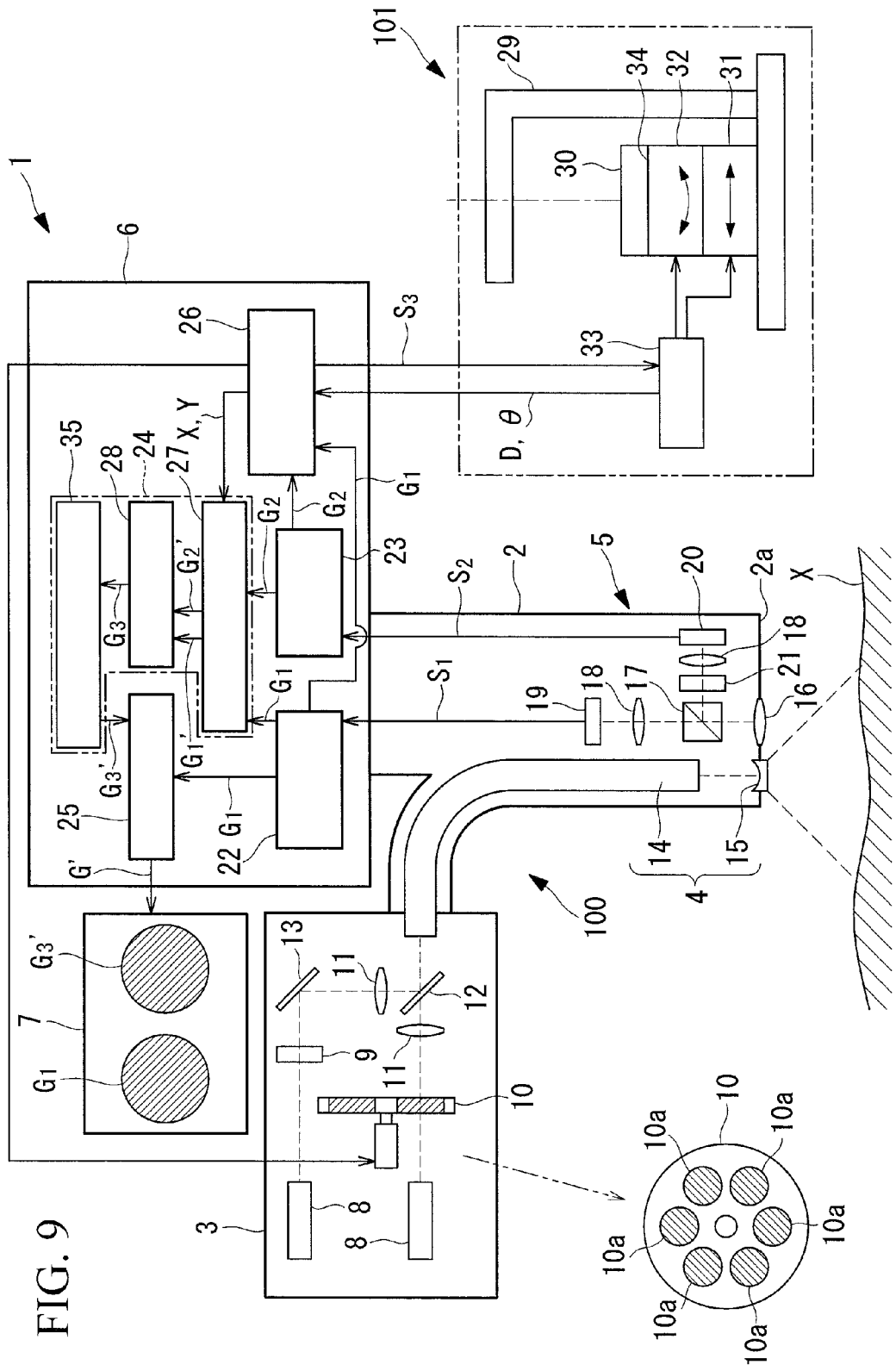
FIG. 9 is a diagram showing the overall configuration of a third modification of the fluoroscopy system in FIG. 1.

As shown in FIG. 9, a post-processing unit 35 that calculates a fluorescence image $G_3'$ by additionally raising the divided value obtained by the division processing unit 28 to the $1/x^{th}$ power may be provided.

The fluorescence intensity of the fluorescence image $G_2$ is proportional to the concentration of a fluorochrome. Specifically, for example, assuming the concentration of a fluorochrome accumulated in a lesion, etc. as C (mol/L), the volume of the specimen as V ($cm^3$), and the cross-sectional area of a plane cut parallel to a top surface of the lesion as S ($cm^2$), the luminance E ($W/cm^2 \cdot sr$) of fluorescence emitted from the lesion is $$E \propto CV/S \approx Ct.$$

Here, t (cm) indicates the thickness of the lesion. Therefore, a gradation value $FL_{before}$ of the captured fluorescence image $G_2$ is approximately proportional to the concentration of the fluorochrome accumulated in the lesion and the thickness of the lesion. In other words, approximately, $FL_{before} \propto Ct$.

However, as described above, in the case of applying pre-processing that raises the luminance value of the fluorescence image $G_2$ to the power of exponent x, a gradation value $FL_{revised}$ of the corrected fluorescence image $G_3$ and Ct have a relationship $$FL_{revised} \propto (Ct)^x,$$

and thus, the fluorescence image $G_3$ does not linearly express the fluorescence concentration in cases other than x=1. Thus, by raising to the $1/x^{th}$ power at the post-processing unit 35, the fluorescence image $G_3'$ that linearly expresses the fluorescence concentration can be acquired. Therefore, the quantitativeness of the fluorescence image can be increased, and the fluorescence concentration and the thickness of a lesion where a fluorochrome has accumulated can also be reflected more accurately.

In this way, by additionally raising to the power of the exponent 1/x after performing processing to reduce the dependencies by raising to the power of the exponent x, it is possible to reduce the distance and angle dependencies while maintaining a proportionality relationship between the luminance of the corrected fluorescence image $G_3$ that is finally acquired and the concentration of a fluorescent substance contained in the subject X.

In this case, because it is preferable that the dependencies on the observation distance D and the observation angle θ be eliminated, including the post-processing by the post-processing unit 35, instead of taking m=ax−cy and n=bx−dy in the above-described example, m=(ax−cy)/x and n=(bx−dy)/x may be used, and the exponents x and y may be set so that m and n serve as permissible limits.

Here, in order for these expressions to have solutions other than x=y=0 regarding x and y, it is necessary to satisfy $$x:y=c:(a-m)=d:(b-n) \qquad (4).$$

Therefore, m and n that satisfy Expression (4) and Expression (3) are set, and, on the basis of the set m and n, x and y should be set from Expression (4).

Here, when m=0, if ϵ=|ad−bc|, from Expression (4), n=(bc−ad)/c=−ϵ/c (when bc−ad<0). Therefore, as described above, by adjusting the wavelengths of the reference image $G_1$ and the fluorescence image $G_2$ so that ϵ is set to the minimum value, the value of n can be further minimized within a range that satisfies Expression (3), and the dependencies of the corrected fluorescence image $G_3$ on the observation distance D and the observation angle θ can be minimized. Here, the size of the aperture of the objective lens 16 or the illumination unit 4 may be set. With such an adjustment, the quantitativeness of the fluorescence image $G_3$ can be further enhanced as much as possible.

In particular, if the wavelength of the illumination light or the size of the aperture of the objective lens 13 or the illumination unit 4 can be set as to obtain the dependency on the observation distance D or the dependency on the observation angle θ that makes E=0, from Expression (4), x and y can be set so that m=n=0 and x:y=c:a=d:b; therefore, the dependencies of the corrected fluorescence image $G_3$ on the observation distance D and the observation angle θ can both be eliminated, and the error can be made almost zero.

Also in this embodiment, although the illumination light wavelength that enables setting of the exponents x and y that minimize ϵ is selected; instead of this, a prescribed threshold $ϵ_{max}$ may be provided, and the illumination light wavelength that enables setting of the exponents x and y that yield ϵ≦$ϵ_{max}$ may be selected.

For example, considering that the absolute values of the exponents a and c expressing the distance dependency are generally larger than the absolute values of the exponents b and d, x and y that yield m=0, for example, x=c and y=a, should be considered. Thus, from Expression (4), n=(bc−ad)/c=−ϵ/c (when bc−ad<0).

Therefore, when $ϵ_{max}$ that satisfies Expression (3) is set, $ϵ_{max}$ must satisfy $$ϵ_{max} ≦ |c| \times \log(1+e_{max})/\log(r_θ)$$

For example, using the exponents a to d obtained by an example experiment, described later, which are
a=−1.518, b=0.514, c=−1.605, d=0.675,
yields ϵ=|ad−bc| 0.20.

The angular field of view of a digestive-organ endoscope is generally about 75° on one side. Therefore, θ can be assumed to be about 75° even at its maximum. In addition, assuming that the maximum permissible error ratio $e_{max}$ is kept at about 20% within this range, $$r_θ = \cos θ_{min}/\cos θ_{max} = \cos 0°/\cos 75° = 3.86.$$

Therefore, $ϵ_{max}$ can be set to, for example $$ϵ_{max} = |c| \times \log(1+e_{max})/\log(r_θ) ≈ 0.217$$

Thus, with this condition, ϵ satisfies $$ϵ=|ad-bc|≈0.20<ϵ_{max}=0.217.$$

This means that quantitativeness within the range of the maximum permissible error ratio $e_{max}$ is obtained at the same time. Therefore, if observation is performed under this condition, it is possible to perform observation in which the quantitativeness is always maintained within the range of the maximum permissible error ratio $e_{max}$.

By optimally adjusting the value of ϵ in this way, it is possible to achieve quantitativeness under conditions like those below the maximum permissible error ratio $e_{max}$.

If ϵ is sufficiently small, for m=0, n=(bc−ad)/c=−ϵ/c (when bc−ad<0) is also sufficiently small. Therefore, even if the maximum permissible error ratio $e_{max}$ is provisionally set to be as small as possible, m and n that satisfy Expressions (3) and (4) exist, and it is possible to set the exponents x and y on the basis of the constants m and n.

Here, an example experiment employing the fluoroscopy system 1 according to this embodiment will be described below with reference to the drawings.

Light in a band including white light and excitation light for a fluorescent agent (wavelength band of 400 to 740 nm) was used as the illumination light, and a reflected-light image of the illumination light reflected at and returning from the surface of a specimen Y was employed as the reference image $G_2$. A fluorescence image generated from a fluorochrome Cy7 injected into the specimen Y was employed as the fluorescence image $G_1$. A removed pig rectum was used as the specimen Y.

Figure 10A:
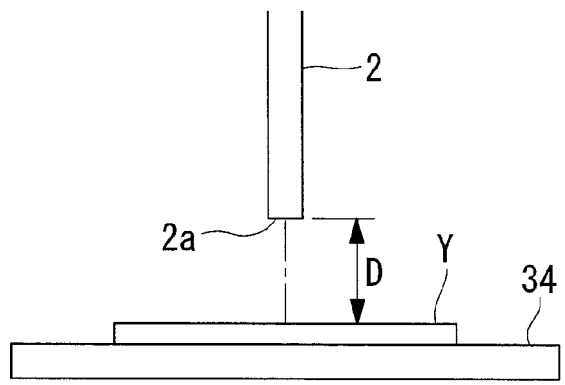
FIG. 10A is a diagram for explaining the measurement of distance dependency in the fluoroscopy system in FIG. 1.
Figure 10B:
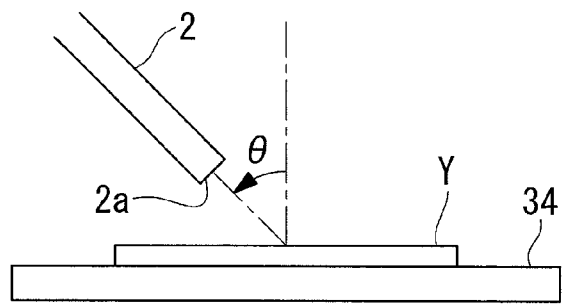
FIG. 10B is a diagram for explaining the measurement of angular dependency in the fluoroscopy system in FIG. 1.

As shown in FIGS. 10A and 10B, the end face 2a of the inserted portion 2 was made to oppose the surface of the specimen Y.

Figure 11A:
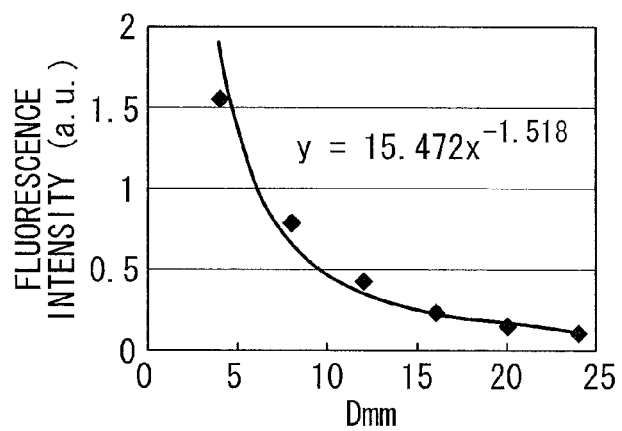
FIG. 11A is a diagram showing a graph of an observation distance characteristic based on the measurement results in FIG. 10A and a power approximation curve based thereon.
Figure 11B:
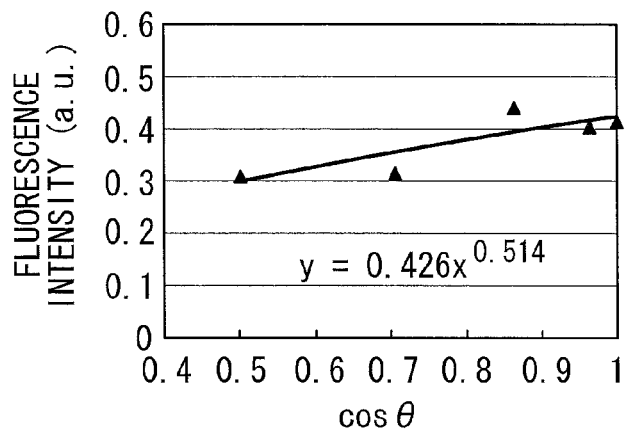
FIG. 11B is a diagram showing a graph of an observation angle characteristic based on the measurement results in FIG. 10B and a power approximation curve based thereon.
Figure 11C:
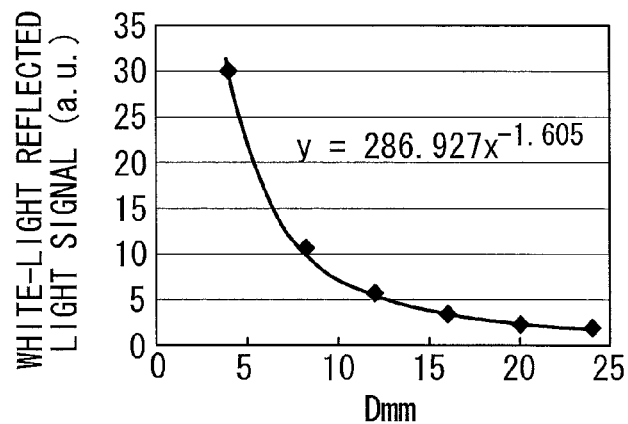
FIG. 11C is a diagram showing a graph of an observation distance characteristic based on the measurement results in FIG. 10A and a power approximation curve based thereon.

For FIG. 10A, which is a measurement diagram for the distance dependency, the reference images $G_1$ and the fluorescence images $G_2$ were acquired by radiating the illumination light and the excitation light at a plurality of observation distances D while increasing the observation distances D by lowering the translation stage 31, at a position where an axial line of the inserted portion 2 was parallel to a normal of a mounting surface 34 of the translation stage 31. As a result, plots showing the observation distance characteristics, such as those shown in FIGS. 11A and 11C, were obtained.

Figure 11D:
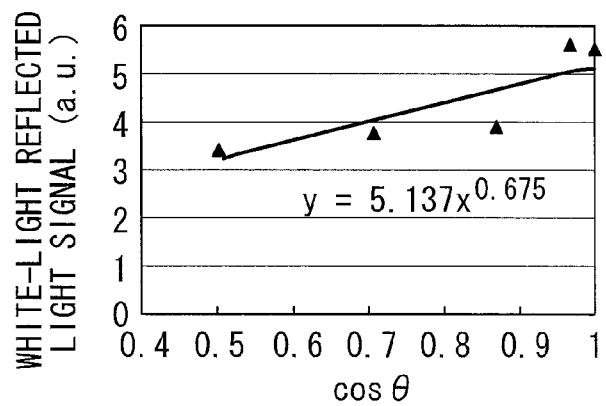
FIG. 11D is a diagram showing a graph of an observation angle characteristic based on the measurement results in FIG. 10B and a power approximation curve based thereon.

For FIG. 10B, which is a measurement diagram for the angular dependency, the reference images $G_1$ and the fluorescence images $G_2$ were acquired by radiating the illumination light and the excitation light at a plurality of observation angles while rotating around a center line disposed on the mounting surface 34, from the position where the axial line of the inserted portion 2 was parallel to the normal of the mounting surface 34. As a result, plots showing the observation angle characteristics, such as those shown in FIGS. 11B and 11D, were obtained.

Then, as shown with solid lines in the figures, when the exponents a and c related to the observation distance and the exponents b and d related to the observation angle were calculated by regression of these plots to a curve $Y=P \cdot X^Q$ (where X is on the horizontal axis, Y is on the vertical axis, P is a constant, and Q is an exponent), a=−1.518, b=0.514, c=−1.605, and d=0.675 were obtained.

Next, a fluoroscopy apparatus 40 according to an embodiment of the present invention will be described below with reference to the drawings.

In the description of this embodiment, portions that are common in configuration with those of the fluoroscopy system 1 according to the above-described embodiment are given the same reference signs, and descriptions thereof are omitted.

Figure 12:
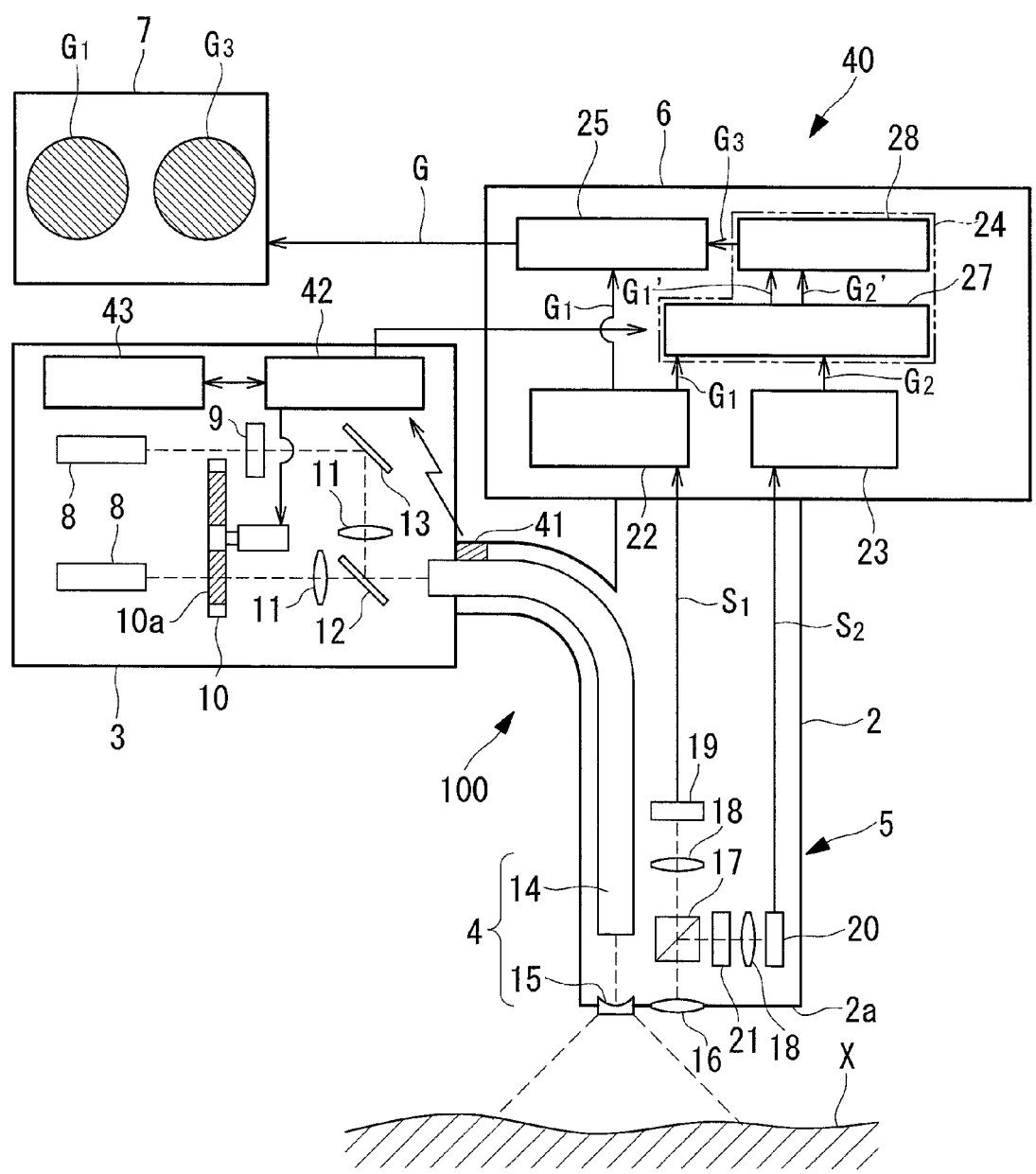
FIG. 12 is a diagram showing the overall configuration of a fluoroscopy apparatus according to an embodiment of the present invention.

As shown in FIG. 12, in the fluoroscopy apparatus 40 according to this embodiment, the light source 3 is provided with the inserted portion (detachable part) 2 in a detachable manner. In this case, by detaching the inserted portion 2 and by exchanging it with another inserted portion 2, various optical systems included in the inserted portion 2, including the objective lens 16, are changed; therefore, the above-described exponents a to d change due to changes in numerical aperture (NA), pupil diameter, etc. of the objective lens 16 or changes in the fluorescence wavelength that is detected, the fluoroscopy target site (stomach tissue, large intestine tissue, etc.), and so on.

Therefore, in this embodiment, an IC chip (identification-information input device) 41 that stores identification information is provided in the inserted portion 2, and, on the light source 3 side to which the inserted portion 2 is attached, a reading device 42 that reads the identification information in the IC chip 41 and a storage unit 43 that stores the identification information and the illumination light wavelength in association with exponents x and y appropriate for each inserted portion 2 are provided. Then, the preprocessing unit 27 receives from the reading device 42 the exponents x and y output from the storage unit 43, which correspond to the identification information of the inserted portion 2, and performs the above-described calculation, and the filter turret (observation-conditions adjusting portion) 10 is driven so that the illumination light wavelength output from the storage unit 43 is achieved.

By doing so, an advantage is afforded in that, even if the inserted portion 2 for the light source 3 is exchanged, the illumination light wavelength that minimizes $\epsilon$ for that inserted portion 2 is selected, optimal exponents x and y are set for the inserted portion 2, and a fluorescence image $G_3$ having high quantitativeness can always be acquired.

Although this embodiment has been illustrated with the IC chip 41 serving as the identification-information input device, instead of this, any other input means using manual input, such as a keyboard, may be used.

Although this embodiment has been illustrated with the filter turret 10 serving as the observation-conditions adjusting portion, the adjustable diaphragm 36 of the objective optical system or the adjustable diaphragm 38 of the illumination optical system may be employed instead.

According to this embodiment, when the inserted portion 2 is attached and detached, changing the observation conditions, and the identification information assigned to the attachable/detachable part is input from the IC chip 41, the observation conditions and exponents x and y stored in association with the identification information in the storage unit 43 can be set. Although this embodiment has been illustrated with the inserted portion 2 serving as the attachable/detachable part, examples of the attachable/detachable part include a scope in an endoscope apparatus, etc. In such a case, the observation conditions to be changed by attaching/detaching the attachable/detachable part include the NA and the pupil diameter of the objective lens 16, the observable fluorescence wavelength, etc., and examples of the observation conditions to be adjusted by the reading apparatus 42 include the wavelength of the illumination unit 4 and the aperture value of the objective lens 16 or the aperture value of the illumination unit 4, at which $\epsilon$ is the threshold $\epsilon_{max}$ or less. For example, when the NA or pupil diameter of the objective lens 16 is changed by replacing the scope, the wavelength of the illumination light is adjusted by the reading apparatus 42, and it is possible to set exponents x and y that reduce the distance dependency and the angular dependency as much as possible, for the changed observation conditions and the adjusted observation conditions, and even if the observation conditions fluctuate, it is possible to perform fluoroscopy with high quantitativeness.

Scattering of and the path taken by the light in the subject X also change due to changes in the illumination light wavelength, the aperture diameter of the objective lens 16, and the beam diameters of the illumination light and excitation light; therefore, the exponents a to d that represent the dependencies on observation distance D and observation angle θ vary, and the exponents x and y for correcting this change. Therefore, by adjusting the observation conditions, it is possible to obtain exponents x and y for obtaining a corrected fluorescence image $G_3$ in which the dependencies on observation distance and observation angle are suitably suppressed, and therefore, fluoroscopy with even higher quantitativeness becomes possible.

REFERENCE SIGNS LIST

X subject
1 fluoroscopy system
2 inserted portion (attachable/detachable part)
3 light source (illumination portion)
4 illumination unit (illumination portion)
10 filter turret (wavelength adjusting portion: observation-conditions adjusting portion)
15 illumination optical system
16 objective lens (objective optical system)
19 image capturing device (return-light imaging portion)
20 image capturing device (fluorescence imaging portion)
24 image-correcting unit
26 dependency-constant determining section (observation-conditions setting unit)
30 standard specimen
31 translation stage (observation-state setting mechanism)
32 tilt stage (observation-state setting mechanism)
36, 38 adjustable diaphragm (observation-conditions adjusting portion)
40, 100 fluoroscopy apparatus
41 IC chip (identification-information input device)
42 reading apparatus (observation-conditions adjusting section)
43 storage unit
101 calibration device

The invention claimed is:
1. A fluoroscopy system comprising:
a fluoroscopy apparatus including
an illumination portion provided with a light source that radiates illumination light and excitation light,
a fluorescence imaging portion that acquires a fluorescence image by imaging fluorescence generated at a subject,
a return-light imaging portion that acquires a reference image by imaging return light returning from the subject, and
an image-correcting unit that corrects the fluorescence image imaged by the fluorescence imaging portion by using the reference image acquired by the return-light imaging portion;

a calibration device connected to the fluoroscopy apparatus and including a standard specimen and an observation-state setting mechanism that sets, in a variable manner, an observation distance and an observation angle of the fluoroscopy apparatus relative to the standard specimen; and an observation-conditions adjusting portion that adjusts observation conditions on the basis of the observation distance and the observation angle set by the calibration device and the fluorescence image and the reference image acquired by imaging the standard specimen with the fluoroscopy apparatus, wherein the observation-conditions adjusting portion calculates values a to d on the basis of the observation distance and the observation angle set by the calibration device and the fluorescence image and the reference image acquired by imaging the standard specimen with the fluoroscopy apparatus and adjusts the observation conditions so that $\epsilon = |ad-bc|$ becomes a prescribed threshold $\epsilon_{max}$ or less, and wherein the image-correcting unit performs the following processing:

$$FL_{revised} = FL_{after}/RL_{after},$$

where $FL_{revised}$ is a luminance value of the corrected fluorescence image, $$FL_{after} = A \times FL_{before}^{x},$$

$$RL_{after} = B \times RL_{before}^{y},$$

$FL_{before}$ and $RL_{before}$ are luminance values of the acquired fluorescence image and reference image, A and B are constants, $$x = (cn-dm)/(bc-ad) \quad (1),$$

$$y = (an-bm)/(bc-ad) \quad (2),$$

a is a value obtained by applying a power approximation to a characteristic of luminance versus distance from the illumination portion to the standard specimen, for the fluorescence image obtained by the fluorescence imaging portion when excitation light of a prescribed intensity is radiated towards the standard specimen, b is a value obtained by applying a power approximation to a characteristic of luminance versus cosine from the illumination portion to the standard specimen, for the fluorescence image obtained by the fluorescence imaging portion when excitation light of a prescribed intensity is radiated towards the standard specimen, c is a value obtained by applying a power approximation to a characteristic of luminance versus distance from the illumination portion to the standard specimen, for the reference image obtained by the return-light imaging portion when illumination light of a prescribed intensity is radiated towards the standard specimen, d is a value obtained by applying a power approximation to a characteristic of luminance versus cosine from the illumination portion to the standard specimen, for the reference image obtained by the return-light imaging portion when illumination light of a prescribed intensity is radiated towards the standard specimen, $$r_D^{|m|} \cdot r_\theta^{|n|} \leq 1 + e_{max} \quad (3)$$

$$r_D = D_{max}/D_{min},$$

$$r_\theta = \cos\theta_{min}/\cos\theta_{max},$$

$D_{max}$ is a presumed maximum observation distance, $D_{min}$ is a presumed minimum observation distance, $\theta_{max}$ is a presumed maximum observation angle, $\theta_{min}$ is a presumed minimum observation angle (where, $0° \leq \theta_{min} < \theta_{max} \leq 90°$), m and n are arbitrary constants that satisfy Expression (3), $e_{max}$ is $(FL_{after}/RL_{after})_{max} \div (FL_{after}/RL_{after})_{min} - 1$;

$(FL_{after}/RL_{after})_{max}$ is a maximum value within a range from the presumed minimum observation distance to the presumed maximum observation distance and within a range from the presumed minimum observation angle to the presumed maximum observation angle, $(FL_{after}/Rt_{after})_{min}$ is a minimum value within a range from the presumed minimum observation distance to the presumed maximum observation distance and within a range from the presumed minimum observation angle to the presumed maximum observation angle, and when bc−ad=0, x and y are set from arbitrary real numbers that satisfy x:y=c:a=d:b.

2. A fluoroscopy system comprising:

a fluoroscopy apparatus including an illumination portion provided with a light source that radiates illumination light and excitation light, a fluorescence imaging portion that acquires a fluorescence image by imaging fluorescence generated at a subject, a return-light imaging portion that acquires a reference image by imaging return light returning from the subject, and an image-correcting unit that corrects the fluorescence image imaged by the fluorescence imaging portion by using the reference image acquired by the return-light imaging portion; a calibration device connected to the fluoroscopy apparatus and including a standard specimen and an observation-state setting mechanism that sets, in a variable manner, an observation distance and an observation angle of the fluoroscopy apparatus relative to the standard specimen; and an observation-conditions adjusting portion that adjusts observation conditions, wherein the observation-conditions adjusting portion calculates values a to d on the basis of the observation angle and the observation distance set by the calibration device and the fluorescence image and the reference image acquired by imaging the standard specimen with the fluoroscopy apparatus and adjusts the observation conditions so that $\epsilon = |ad-bc|$ becomes a prescribed threshold $\epsilon_{max}$ or less, and wherein the image-correcting unit performs the following processing:

$$FL_{revised} = (FL_{after}/RL_{after})^{1/x},$$

where $FL_{revised}$ is a luminance value of the corrected fluorescence image, $$FL_{after} = A \times RL_{before}^{x},$$

$$RL_{after} = B \times RL_{before}^{y},$$

$FL_{before}$ and $RL_{before}$ are luminance values of the acquired fluorescence image and reference image, A and B are constants, $$x:y = c:(a-m) = d:(b-n) \quad (4),$$

a is a value obtained by applying a power approximation to a characteristic of luminance versus distance from the illumination portion to the standard specimen, for the fluorescence image obtained by the fluorescence imaging portion when excitation light of a prescribed intensity is radiated towards the standard specimen, b is a value obtained by applying a power approximation to a characteristic of luminance versus cosine from the illumination portion to the standard specimen, for the fluorescence image obtained by the fluorescence imaging portion when excitation light of a prescribed intensity is radiated towards the standard specimen, c is a value obtained by applying a power approximation to a characteristic of luminance versus distance from the illumination portion to the standard specimen, for the reference image obtained by the return-light imaging portion when illumination light of a prescribed intensity is radiated towards the standard specimen, d is a value obtained by applying a power approximation to a characteristic of luminance versus cosine from the illumination portion to the standard specimen, for the reference image obtained by the return-light imaging portion when illumination light of a prescribed intensity is radiated towards the standard specimen, $$r_D^{|m|} \cdot r_\theta^{|n|} \leq 1 + e_{max} \qquad (3)$$

$$r_D = D_{max}/D_{min},$$

$$r_\theta = \cos\theta_{min}/\cos\theta_{max},$$

$D_{max}$ is a presumed maximum observation distance,
$D_{min}$ is a presumed minimum observation distance,
$\theta_{max}$ is a presumed maximum observation angle,
$\theta_{min}$ is a presumed minimum observation angle (where, $0° \leq \theta_{min} < \theta_{max} \leq 90°$),
m and n are arbitrary constants that satisfy Expressions (3) and (4),
$e_{max}$ is $(FL_{after}/RL_{after})_{max} \div (FL_{after}/RL_{after})_{min} - 1$;
$(FL_{after}/RL_{after})_{max}$ is a maximum value within a range from the presumed minimum observation distance to the presumed maximum observation distance and within a range from the presumed minimum observation angle to the presumed maximum observation angle, and
$(FL_{after}/Rt_{after})_{min}$ is a minimum value within a range from the presumed minimum observation distance to the presumed maximum observation distance and within a range from the presumed minimum observation angle to the presumed maximum observation angle.

3. A fluoroscopy system according to claim 1, wherein m=0.

4. A fluoroscopy system according to claim 1, wherein the observation-conditions adjusting portion is a wavelength-adjusting portion that adjusts the wavelength of the illumination light.

5. A fluoroscopy system according to claim 1, further comprising an objective optical system that collects the fluorescence and return light returning from the subject,
wherein the observation-conditions adjusting portion is an adjustable diaphragm provided in the objective optical system.

6. A fluoroscopy system according to claim 1, wherein the observation-conditions adjusting portion is an adjustable diaphragm that adjusts a beam diameter of the illumination light and the excitation light.

7. A fluoroscopy apparatus comprising:
an illumination portion provided with a light source that radiates illumination light and excitation light;
a fluorescence imaging portion that acquires a fluorescence image by imaging fluorescence generated at a subject;
a return-light imaging portion that acquires a reference image by imaging return light returning from the subject;
an image-correcting unit that corrects the fluorescence image imaged by the fluorescence imaging portion by using the reference image acquired by the return-light imaging portion;
an attachable/detachable part that is attached/detached to change observation conditions;
an identification-information input device that inputs identification information assigned to the attachable/detachable part;
a storage unit that stores the identification information, exponents x and y, and the observation conditions in association with each other; and
an observation-conditions adjusting portion that sets the observation conditions to the observation conditions stored in the storage unit in association with the identification information input by the identification-information input device when the attachable/detachable part is connected,
wherein the image-correcting unit performs the following processing using the exponents x and y stored in the storage unit in association with the identification information input by the identification-information input device:

$$FL_{revised} = FL_{after}/RL_{after},$$

where
$FL_{revised}$ is a luminance value of the corrected fluorescence image, $$FL_{after} = A \times FL_{before}^{x},$$

$$RL_{after} = B \times RL_{before}^{y},$$

$FL_{before}$ and $RL_{before}$ are luminance values of the acquired fluorescence image and reference image,
A and B are constants, $$x = (cn - dm)/(bc - ad) \qquad (1),$$

$$y = (an - bm)/(bc - ad) \qquad (2),$$

a is a value obtained by applying a power approximation to a characteristic of luminance versus distance from the illumination portion to the subject, for the fluorescence image obtained by the fluorescence imaging portion when excitation light of a prescribed intensity is radiated towards the subject, b is a value obtained by applying a power approximation to a characteristic of luminance versus cosine from the illumination portion to the subject, for the fluorescence image obtained by the fluorescence imaging portion when excitation light of a prescribed intensity is radiated towards the subject, c is a value obtained by applying a power approximation to a characteristic of luminance versus distance from the illumination portion to the subject, for the reference image obtained by the return-light imaging portion when illumination light of a prescribed intensity is radiated towards the subject, d is a value obtained by applying a power approximation to a characteristic of luminance versus cosine from the illumination portion to the subject, for the reference image obtained by the return-light imaging portion when illumination light of a prescribed intensity is radiated towards the subject, $$r_D^{|m|} \cdot r_\theta^{|n|} \leq 1 + e_{max} \qquad (3)$$

$$r_D = D_{max}/D_{min},$$

$$r_\theta = \cos\theta_{min}/\cos\theta_{max},$$

$D_{max}$ is a presumed maximum observation distance,
$D_{min}$ is a presumed minimum observation distance,
$\theta_{max}$ is a presumed maximum observation angle,
$\theta_{min}$ is a presumed minimum observation angle (where, $0° \leq \theta_{min} < \theta_{max} \leq 90°$),
m and n are arbitrary constants that satisfy Expression (3)
$e_{max}$ is $(FL_{after}/RL_{after})_{max} \div (FL_{after}/RL_{after})_{min} - 1$;
$(FL_{after}/RL_{after})_{max}$ is a maximum value within a range from the presumed minimum observation distance to the presumed maximum observation distance and within a range from the presumed minimum observation angle to the presumed maximum observation angle,
$(FL_{after}/Rt_{after})_{min}$ is a minimum value within a range from the presumed minimum observation distance to the presumed maximum observation distance and within a range from the presumed minimum observation angle to the presumed maximum observation angle, and
when bc−ad=0, x and y are set from arbitrary real numbers that satisfy x:y=c:a=d:b.

8. A fluoroscopy apparatus comprising:
an illumination portion provided with a light source that radiates illumination light and excitation light;
a fluorescence imaging portion that acquires a fluorescence image by imaging fluorescence generated at a subject;
a return-light imaging portion that acquires a reference image by imaging return light returning from the subject;
an image-correcting unit that corrects the fluorescence image imaged by the fluorescence imaging portion by using the reference image acquired by the return-light imaging portion;
an attachable/detachable part that is attached/detached to change observation conditions;
an identification-information input device that inputs identification information assigned to the attachable/detachable part;
a storage unit that stores the identification information, exponents x and y, and the observation conditions in association with each other; and
an observation-conditions adjusting portion that sets the observation conditions to the observation conditions stored in the storage unit in association with the identification information input by the identification-information input device when the attachable/detachable part is connected;
wherein, the image-correcting unit performs the following processing using the exponents x and y stored in the storage unit in association with the identification information input by the identification-information input device:

$$FL_{revised} = (FL_{after}/RL_{after})^{1/x},$$

where
$FL_{revised}$ is a luminance value of the corrected fluorescence image, $$FL_{after} = A \times FL_{before}^{x},$$

$$RL_{after} = B \times RL_{before}^{y},$$

$FL_{before}$ and $RL_{before}$ are luminance values of the acquired fluorescence image and reference image,
A and B are constants, $$x:y = c:(a-m) = d:(b-n) \qquad (4),$$

a is a value obtained by applying a power approximation to a characteristic of luminance versus distance from the illumination portion to the subject, for the fluorescence image obtained by the fluorescence imaging portion when excitation light of a prescribed intensity is radiated towards the subject,
b is a value obtained by applying a power approximation to a characteristic of luminance versus cosine from the illumination portion to the subject, for the fluorescence image obtained by the fluorescence imaging portion when excitation light of a prescribed intensity is radiated towards the subject,
c is a value obtained by applying a power approximation to a characteristic of luminance versus distance from the illumination portion to the subject, for the reference image obtained by the return-light imaging portion when illumination light of a prescribed intensity is radiated towards the subject,
d is a value obtained by applying a power approximation to a characteristic of luminance versus cosine from the illumination portion to the subject, for the reference image obtained by the return-light imaging portion when illumination light of a prescribed intensity is radiated towards the subject, $$r_D^{|m|} \cdot r_\theta^{|n|} \leq 1 + e_{max} \qquad (3)$$

$$r_D = D_{max}/D_{min},$$

$$r_\theta = \cos\theta_{min}/\cos\theta_{max},$$

$D_{max}$ is a presumed maximum observation distance,
$D_{min}$ is a presumed minimum observation distance,
$\theta_{max}$ is a presumed maximum observation angle,
$\theta_{min}$ is a presumed minimum observation angle (where, $0° \leq \theta_{min} < \theta_{max} \leq 90°$),
m and n are arbitrary constants that satisfy Expressions (3) and (4),
$e_{max}$ is $(FL_{after}/RL_{after})_{max} \div (FL_{after}/RL_{after})_{min} - 1$;
$(FL_{after}/RL_{after})_{max}$ is a maximum value within a range from the presumed minimum observation distance to the presumed maximum observation distance and within a range from the presumed minimum observation angle to the presumed maximum observation angle, and
$(FL_{after}/RL_{after})_{min}$ is a minimum value within a range from the presumed minimum observation distance to the presumed maximum observation distance and within a range from the presumed minimum observation angle to the presumed maximum observation angle.

9. A fluoroscopy apparatus according to claim 7, wherein m=0.

10. A fluoroscopy apparatus according to claim 7, wherein the observation-conditions adjusting portion is a wavelength-adjusting portion that adjusts the wavelength of the illumination light.

11. A fluoroscopy apparatus according to claim 7, further comprising an objective optical system that collects the fluorescence and the return light returning from the subject,
wherein the observation-conditions adjusting portion is an adjustable diaphragm provided in the objective optical system.

12. A fluoroscopy apparatus according to claim 7, wherein the observation-conditions adjusting portion is an adjustable diaphragm that adjusts a beam diameter of the illumination light and the excitation light.

13. A fluoroscopy method comprising:
irradiating a standard specimen with illumination light and excitation light while varying an observation distance and an observation angle, acquiring a plurality of fluorescence images at different observation distances and/or observation angles by imaging fluorescence generated at the standard specimen, acquiring a plurality of reference images at different observation distances and/or observation angles by imaging return light returning from the standard specimen, calculating values a to d on the basis of the acquired plurality of fluorescence images and reference images, and adjusting observation conditions so that $\epsilon=|ad-bc|$ becomes a prescribed threshold $\epsilon_{max}$ or less;

irradiating a subject with illumination light and excitation light; and performing the following correction processing on a fluorescence image acquired by imaging fluorescence generated at the subject by using a reference image acquired by imaging return light returning from the subject:

$$FL_{revised}=FL_{after}/RL_{after},$$

where $FL_{revised}$ is a luminance value of the corrected fluorescence image, $$FL_{after}=A \times FL_{before}^{x},$$

$$RL_{after}=B \times RL_{before}^{y},$$

$FL_{before}$ and $RL_{before}$ are luminance values of the acquired fluorescence image and reference image, A and B are constants, $$x=(cn-dm)/(bc-ad) \qquad (1),$$

$$y=(an-bm)/(bc-ad) \qquad (2),$$

a is a value obtained by applying a power approximation to a characteristic of luminance versus distance from the illumination portion to the standard specimen, for the fluorescence image obtained by a fluorescence imaging portion when excitation light of a prescribed intensity is radiated towards the standard specimen, b is a value obtained by applying a power approximation to a characteristic of luminance versus cosine from the illumination portion to the standard specimen, for the fluorescence image obtained by the fluorescence imaging portion when excitation light of a prescribed intensity is radiated towards the standard specimen, c is a value obtained by applying a power approximation to a characteristic of luminance versus distance from the illumination portion to the standard specimen, for the reference image obtained by a return-light imaging portion when illumination light of a prescribed intensity is radiated towards the standard specimen, d is a value obtained by applying a power approximation to a characteristic of luminance versus cosine from the illumination portion to the standard specimen, for the reference image obtained by the return-light imaging portion when illumination light of a prescribed intensity is radiated towards the standard specimen, $$r_D^{|m|} \cdot r_\theta^{|n|} \leq 1+e_{max} \qquad (3)$$

$$r_D=D_{max}/D_{min},$$

$$r_\theta=\cos\theta_{min}/\cos\theta_{max},$$

$D_{max}$ is a presumed maximum observation distance,
$D_{min}$ is a presumed minimum observation distance,
$\theta_{max}$ is a presumed maximum observation angle,
$\theta_{min}$ is a presumed minimum observation angle (where, $0° \leq \theta_{min} < \theta_{max} \leq 90°$),
m and n are arbitrary constants that satisfy Expression (3),
$e_{max}$ is $(FL_{after}/RL_{after})_{max} \div (FL_{after}/RL_{after})_{min}-1$;

$(FL_{after}/RL_{after})_{max}$ is a maximum value within a range from the presumed minimum observation distance to the presumed maximum observation distance and within a range from the presumed minimum observation angle to the presumed maximum observation angle, $(FL_{after}/Rt_{after})_{min}$ is a minimum value within a range from the presumed minimum observation distance to the presumed maximum observation distance and within a range from the presumed minimum observation angle to the presumed maximum observation angle, and when bc−ad=0, x and y are set from arbitrary real numbers that satisfy x:y=c:a=d:b.

14. A fluoroscopy method comprising:

irradiating a standard specimen with illumination light and excitation light while varying an observation distance and an observation angle, acquiring a plurality of fluorescence images at different observation distances and/or observation angles by imaging fluorescence generated at the standard specimen, acquiring a plurality of reference images at different observation distances and/or observation angles by imaging return light returning from the standard specimen, calculating values a to d on the basis of the acquired plurality of fluorescence images and reference images, and adjusting observation conditions so that $\epsilon=|ad-bc|$ becomes a prescribed threshold $\epsilon_{max}$ or less;

irradiating a subject with illumination light and excitation light; and performing the following correction processing on a fluorescence image acquired by imaging fluorescence generated at the subject by using a reference image acquired by imaging return light returning from the subject:

$$FL_{revised}=(FL_{after}/RL_{after})^{1/x},$$

where $FL_{revised}$ is a luminance value of the corrected fluorescence image, $$FL_{after}=A \times FL_{before}^{x},$$

$$RL_{after}=B \times RL_{before}^{y},$$

$FL_{before}$ and $RL_{before}$ are luminance values of the acquired fluorescence image and reference image, A and B are constants, $$x:y=c:(a-m)=d:(b-n) \qquad (4),$$

a is a value obtained by applying a power approximation to a characteristic of luminance versus distance from the illumination portion to the standard specimen, for the fluorescence image obtained by a fluorescence imaging portion when excitation light of a prescribed intensity is radiated towards the standard specimen, b is a value obtained by applying a power approximation to a characteristic of luminance versus cosine from the illumination portion to the standard specimen, for the fluorescence image obtained by the fluorescence imaging portion when excitation light of a prescribed intensity is radiated towards the standard specimen, c is a value obtained by applying a power approximation to a characteristic of luminance versus distance from the illumination portion to the standard specimen, for the reference image obtained by a return-light imaging portion when illumination light of a prescribed intensity is radiated towards the standard specimen, d is a value obtained by applying a power approximation to a characteristic of luminance versus cosine from the illumination portion to the standard specimen, for the reference image obtained by the return-light imaging portion when illumination light of a prescribed intensity is radiated towards the standard specimen, $$r_D{}^{|m|} \cdot r_\theta{}^{|n|} \leq 1 + e_{max} \qquad (3)$$

$$r_D = D_{max}/D_{min},$$

$$r_\theta = \cos\theta_{min}/\cos\theta_{max},$$

$D_{max}$ is a presumed maximum observation distance,
$D_{min}$ is a presumed minimum observation distance,
$\theta_{max}$ is a presumed maximum observation angle,
$\theta_{min}$ is a presumed minimum observation angle (where, $0° \leq \theta_{min} < \theta_{max} \leq 90°$),
m and n are arbitrary constants that satisfy Expressions (3) and (4),
$\theta_{max}$ is $(FL_{after}/RL_{after})_{max} \div (FL_{after}/RL_{after})_{min} - 1$;
$(FL_{after}/RL_{after})_{max}$ is a maximum value within a range from the presumed minimum observation distance to the presumed maximum observation distance and within a range from the presumed minimum observation angle to the presumed maximum observation angle,
$(FL_{after}/Rt_{after})_{min}$ is a minimum value within a range from the presumed minimum observation distance to the presumed maximum observation distance and within a range from the presumed minimum observation angle to the presumed maximum observation angle.

15. A fluoroscopy system according to claim 2, wherein m=0.

16. A fluoroscopy system according to claim 2, wherein the observation-conditions adjusting portion is a wavelength-adjusting portion that adjusts the wavelength of the illumination light.

17. A fluoroscopy system according to claim 2, further comprising an objective optical system that collects the fluorescence and return light returning from the subject,
wherein the observation-conditions adjusting portion is an adjustable diaphragm provided in the objective optical system.

18. A fluoroscopy system according to claim 2, wherein the observation-conditions adjusting portion is an adjustable diaphragm that adjusts a beam diameter of the illumination light and the excitation light.

19. A fluoroscopy apparatus according to claim 8, wherein m=0.

20. A fluoroscopy apparatus according to claim 8, wherein the observation-conditions adjusting portion is a wavelength-adjusting portion that adjusts the wavelength of the illumination light.

21. A fluoroscopy apparatus according to claim 8, further comprising an objective optical system that collects the fluorescence and the return light returning from the subject,
wherein the observation-conditions adjusting portion is an adjustable diaphragm provided in the objective optical system.

22. A fluoroscopy apparatus according to claim 8, wherein the observation-conditions adjusting portion is an adjustable diaphragm that adjusts a beam diameter of the illumination light and the excitation light.

* * * * *